(12) United States Patent
Roush et al.

(10) Patent No.: US 11,666,578 B2
(45) Date of Patent: Jun. 6, 2023

(54) SMALL MOLECULE INHIBITORS OF CDK12/CDK13

(71) Applicant: The Scripps Research Institute, La Jolla, CA (US)

(72) Inventors: William R. Roush, Jupiter, FL (US); Derek R. Duckett, Jupiter, FL (US); Andrii Monastyrskyi, Jupiter, FL (US)

(73) Assignees: THE UNIVERSITY OF FLORIDA RESEARCH FOUNDATION, INC., Gainseville, FL (US); THE UNIVERSITY OF FLORIDA BOARD OF TRUSTEES, Gainesville, FL (US)

( * ) Notice: Subject to any disclaimer, the term of this patent is extended or adjusted under 35 U.S.C. 154(b) by 140 days.

(21) Appl. No.: 17/053,652

(22) PCT Filed: May 7, 2019

(86) PCT No.: PCT/US2019/031116
§ 371 (c)(1),
(2) Date: Nov. 6, 2020

(87) PCT Pub. No.: WO2019/217421
PCT Pub. Date: Nov. 14, 2019

(65) Prior Publication Data
US 2021/0186979 A1  Jun. 24, 2021

Related U.S. Application Data

(60) Provisional application No. 62/668,628, filed on May 8, 2018.

(51) Int. Cl.
*A61K 31/5377* (2006.01)

(52) U.S. Cl.
CPC .............................. *A61K 31/5377* (2013.01)

(58) Field of Classification Search
None
See application file for complete search history.

(56) References Cited

U.S. PATENT DOCUMENTS

| 9,493,464 B2 | 11/2016 | Roush et al. |
| 2008/0004270 A1 | 1/2008 | Gill et al. |

FOREIGN PATENT DOCUMENTS

| WO | WO-2017066055 A1 | 4/2017 |
| WO | WO-2019217421 A1 | 11/2019 |

OTHER PUBLICATIONS

Bibian et al., Bioorganic & Medicinal Chemistry Letters (2013), 23, pp. 4374-4380.*

"International Application No. PCT/US2019/031116, International Preliminary Report on Patentability dated Nov. 19, 2020", (Nov. 19, 2020), 7 pgs.

"International Application No. PCT/US2019/031116, International Search Report and Written Opinion dated Sep. 5, 2019", (Sep. 5, 2019), 10 pgs.

Bibian, Mathieu, et al., "Development of highly selective casein kinase 1 d/1 e (CK1d/e) inhibitors with potent antiproliferative properties", Bioorg Med Chem Lett. Aug. 1, 2013; 23(15): 4374-4380, (Aug. 1, 2013), 4374-4380.

Bielawski, Marcin, et al., "One-Pot Synthesis and Applications of N-Heteroaryl Iodonium Salts", ChemistryOpen 2014, 3(1), 19-22, (Jan. 23, 2014), 19-22.

Bielawski, Marcin, et al., "Regiospecific One-Pot Synthesis of Diaryliodonium Tetrafluoroborates from Arylboronic Acids and Aryl Iodides", J. Org. Chem. 2008, 73, 12, 4602-4607, (May 28, 2008), 4602-4607.

Bosken, Christian A., et al., "The structure and substrate specificity of human Cdk12/Cyclin K", Nat Commun. Mar. 24, 2014; 5: 3505., (Mar. 24, 2014), 14 pgs.

Ding, S., et al., "Expanding the diversity of purine libraries", Tetrahedron Letters, 41 (50), (Dec. 20, 2001), 8751-8755.

Jorda, Radek, "Cyclin-dependent kinase Inhibitors Inspired by Roscovitine: Purine Bioisosteres", Current Pharmaceutical Design, 2012, vol. 18, p. 2974-2980, (2012), 2974-2980.

(Continued)

*Primary Examiner* — Brian J Davis

(57) ABSTRACT

The invention provides compounds and methods of inhibiting a cyclin-dependent kinase, comprising contacting the cyclin-dependent kinase and an effective amount or concentration of a compound of formula (I) wherein variables are as defined herein. Compounds of formula (I) can be highly selective inhibitors of cyclin-dependent kinases such as CDK12/13, relative to other kinases such as casein kinases, such as CK1δ/ε. Compounds can be used in treatment of cancers, such as breast cancer, brain cancer and ovarian cancer.

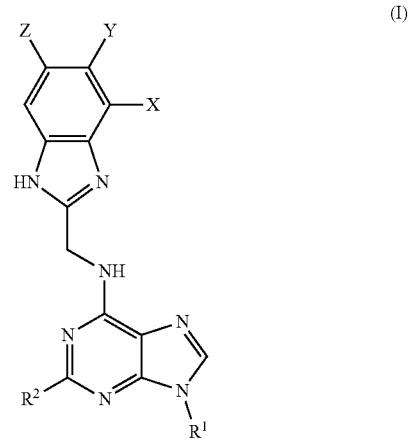

14 Claims, 11 Drawing Sheets
Specification includes a Sequence Listing.

(56) References Cited

OTHER PUBLICATIONS

Monastyrskyi, Andrii, et al., "Development of dual casein kinase 1d/1e (CK1d/e) inhibitors for treatment of breast cancer", Bioorg Med Chem. Feb. 1, 2018; 26(3): 590-602. doi:10.1016/j.bmc.2017.12.020, (Feb. 1, 2018), 590-602.

Niu, Hong-Ying, et al., "CuBr catalyzed C-N cross coupling reaction of purines and diaryliodonium salts to 9-arylpurines", Org Biomol Chem. Jul. 21, 2011;9(14):5039-42. doi: 10.1039/c1ob05333g. Epub Jun. 9, 2011 [abstract only], (Jul. 21, 2011), 5039-42.

* cited by examiner

Comp 10

|  | % inh @ 10 µM |
|---|---:|
| CDK4 | 99 |
| CDK7 | 98 |
| CDK13 | 12 |
|  | IC$_{50}$ [nM] |
| CK1δ | 4 |
| CDK4 | 280 |
| CDK6 | 1240 |

Figure 2a

| | SR-3029 | | Comp 1 | | Comp 3 | |
|---|---|---|---|---|---|---|
| | IC$_{50}$ [nM] | % inh @10 μM | IC$_{50}$ [nM] | % inh @10 μM | IC$_{50}$ [nM] | % inh @10 μM |
| CDK13 | 10 | 100 | 5 | 100 | 4 | 100 |
| CDK12 | 23 | | 14 | | 22 | |
| CDK11 | | 0 | | 0 | | 23 |
| CDK2 | | 1 | | 6 | | 3 |
| CDK3 | | 6 | | 3 | | 8 |
| CDK4-cyclinD1 | 575 | 97 | | 99 | | 99 |
| CDK4-cyclinD3 | | 95 | | 99 | | 99 |
| CDK5 | | 18 | | 9 | | 7 |
| CDK6-cyclinD1 | 428 | | | | | |
| CDK7 | | 72 | | 69 | | 69 |
| CDK8 | | 22 | | 0 | | 40 |
| CDK9 | | 69 | | 43 | | 64 |
| CDKL1 | | 8 | | 16 | | 16 |
| CDKL2 | | 0 | | 0 | | 2 |
| CDKL3 | | 5 | | 0 | | 0 |
| CDKL5 | | 0 | | 0 | | 1 |

Figure 2b

| Kinase | IC$_{50}$ [nM] | % inh @10 µM |
|---|---|---|
| CDK13 | 5 | |
| CDK12 | 98 | |
| AKT1 | | 1 |
| AKT2 | | 2 |
| AKT3 | | 7 |
| AXL | | 5 |
| c-MET | | 0 |
| CDK4/cyclin D1 | 10000 | 48 |
| CDK4/cyclin D3 | | 48 |
| CDK6/cyclin D1 | 5100 | 84 |
| CDK6/cyclin D3 | | 54 |
| CDK9 | 10000 | |
| EGFR | | 4 |
| ERBB2/HER2 | | 4 |
| ERK1 | | 0 |
| ERK2/MAPK1 | | 8 |
| ERK5/MAPK7 | | 0 |
| ERK5/MAPK7 | | 0 |
| ERK7/MAPK15 | | 0 |
| GSK3a | 1200 | 91 |
| GSK3b | 810 | 97 |
| MEK1 | | 5 |
| MEK2 | | 9 |

| Kinase | % inh |
|---|---|
| CDK12 | 100 |
| LRRK2 | 100 |
| GSK3B (GSK3 beta) | 89 |
| GSK3A (GSK3 alpha) | 82 |
| SPHK2 | 68 |
| PIK3C2B (PI3K-C2 beta) | 64 |
| CDK9/cyclin T1 | 64 |
| SPHK1 | 54 |
| CSNK1E (CK1 epsilon) | 49 |
| BRAF V599E | 46 |
| PRKCB2 (PKC beta II) | 46 |

SMALL MOLECULE INHIBITORS OF CDK12/CDK13

CROSS-REFERENCE TO RELATED APPLICATIONS

This application is a U.S. national stage filing under 35 U.S.C. § 371 from International Application No. PCT/US2019/031116, filed on May 7, 2019, and published as WO2019/217421 on Nov. 14, 2019, which claims the priority of U.S. provisional patent application Ser. No. 62/668,628, filed May 8, 2018, the benefit of priority of each of which is claimed herein, and which applications and publication are hereby incorporated herein by reference in their entirety.

Reference is made to PCT/US16/055436, filed Oct. 5, 2016, and published as WO17/066,055, Apr. 20, 2017, by William R. Roush, Derek R. Duckett, John L. Cleveland, and Laura H. Rosenberg, and to U.S. Pat. No. 9,493,464 by William R. Roush, Ronald Rahaim, and Mathieu Bibian, issued Nov. 15, 2016, the disclosures of which are incorporated herein by reference in their entireties.

STATEMENT OF GOVERNMENT SUPPORT

This invention was made with government support under 5R01CA175094 and 1F32CA200105 awarded by the National Institutes of Health. The government has certain rights in the invention.

BACKGROUND

Cyclin-dependent kinases 12 and 13 (CDK12 and CDK13) are Ser/Thr protein kinase members of the large CDK family (>20 different human CDKs and CDK-like enzymes) that regulate different phases of the transcription cycle from transcription initiation to elongation and termination.[1] CDKs are key regulators of cell proliferation and five members of this family—CDK7, CDK8, CDK9, CDK12 and CDK13—have been described as transcription-regulating kinases playing pivotal roles in controlling regulation of transcription and posttranscriptional RNA processing. Specifically, CDK12 and CDK13 associated with cyclin K (CycK) phosphorylate serine at position 2 (Ser2) of the C-terminal domain (CTD) of RNA polymerase II.

Depletion of CDK12/CycK or CDK13/CycK does not affect the rate of global transcription; rather, CDK12/CycK acts as the limiting factor for the transcription of a small subset of genes that involved in the DNA damage response pathway where CDK13/CycK affects expression of genes involved in growth signaling pathways.[2] Reported data suggest that inhibition of CDK12 and CDK13 may be an effective strategy for targeting certain cancers.[3, 4] Human CDK12 and CDK13 share 43% sequence identity and an expanded region of serine —arginine motifs in their N-terminal regions linking the kinases to the SR protein family involved in RNA processing and pre-mRNA splicing.[5, 6] However, their exact roles in the above processes are not fully understood. CDK12 mutations have been reported in many cancers such as breast cancer including triple negative breast cancer as well as high-grade serous ovarian carcinoma rendering CDK12 a promising target for drug development. To the best of our knowledge, the only selective inhibitor of CDK12/13 reported so far—THZ531, which covalently targets a remote cysteine residue outside of the kinase ATP binding pocket.[7] Thus, there is an urgent need for the development of selective, non-covalent inhibitors of CDK12/13 to fully explore the therapeutic potential of targeting these kinases either individually or alone, or in combination with radiation treatment and/or other chemotherapies.

SUMMARY

The chemical series disclosed here have the potential for use in targeted treatment of variety of cancers including breast cancer, brain cancer and ovarian cancer. Different human cancers involve deregulation of transcription-CDKs processes. CDK9 was considered the only transcription-CDK with a causative role in cancer until recently. New evidence supports the importance of CDK12 in transcription and RNA processing, maintaining genomic stability/integrity and tumorigenesis.[3] This chemical series offers new opportunities for treatment of cancers with altered CDK12 activity.

The invention is directed, in various embodiments, to the medical use of inhibitors of cyclin-dependent kinases, such as cyclin-dependent kinases 12 and 13. These CDK inhibitors of the invention can be highly selective, having high affinities, in low nanomolar ranges, to cyclin-dependent kinases such as CDK12/13, while having low affinity (micromolar and higher) for other kinases such as casein kinases, e.g., casein kinases 15/E.

In various embodiments, the invention provides a method of inhibiting a cyclin-dependent kinase, comprising contacting the cyclin-dependent kinase and an effective amount or concentration of a compound of formula (I)

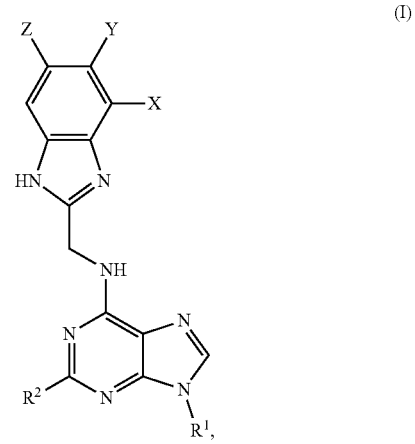

(I)

wherein $R^1$ is aryl or heteroaryl optionally mono- or independently multi-substituted with J;

wherein J independently at each occurrence is selected from the group consisting of F, Cl, Br, I, OR, CN, $CF_3$, $OCF_3$, $NO_2$, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, $N(R)N(R)CON(R_2)$, $N(R)SO_2R$, $N(R)SO_2N(R)_2$, N(R)C(O)OR, N(R)C(O)R, N(R)C(S)R, $N(R)C(O)N(R)_2$, N(R)C(S)N(R)_2, N(COR)COR, N(OR)R, $C(=NH)N(R_2)$, C(O)N(OR) R, C(=NOR)R, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with R, (C$_{1-6}$)alkyl, (C$_{2-6}$)alkenyl, (C$_{2-6}$)alkynyl, (C$_{1-6}$)haloalkyl, (C$_{1-6}$)alkoxy, (C$_{1-6}$)haloalkoxy, cycloalkyl(C$_{0-6}$)alkyl, heterocyclyl(C$_{0-6}$)alkyl, aryl(C$_{0-6}$)alkyl, or heteroaryl (C$_{0-6}$)alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a (C$_{3-8}$)heterocyclyl mono- or multi-substituted with R; optionally further comprising 1-3 additional heteroatoms selected from the group consisting of O, N, S, S(O) and S(O)$_2$;

wherein R is independently at each occurrence is selected from the group consisting of hydrogen, deuterium, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 J$^R$; or wherein two R groups together with a nitrogen atom or with two adjacent nitrogen atoms to which they are bonded can together form a (C$_{3-8}$)heterocyclyl substituted with 0-3 J$^R$; optionally further comprising 1-3 additional heteroatoms selected from the group consisting of O, N, S, S(O) and S(O)$_2$;

wherein any cycloalkyl, aryl, heterocyclyl, or heteroaryl can be fused, bridged, or in a spiro configuration with one or more additional optionally mono- or independently multi-substituted cycloalkyl, aryl, heterocyclyl, and heteroaryl, monocyclic, bicyclic, bicyclic or polycyclic, saturated, partially unsaturated, or aromatic rings;

R$^2$ is NR$^3$R$^4$, wherein R$^3$ and R$^4$ are each independently H or (C1-C6)alkyl, the alkyl being optionally substituted with hydroxyl or with N(R$^6$)$_2$ on any carbon atom thereof other than a carbon atom bonded directed to the nitrogen atom of NR$^3$R$^4$, or R$^3$ and R$^4$ together with the nitrogen atom to which they are bonded form a 5- to 7-membered heterocyclyl ring optionally comprising 1 or 2 additional heteroatoms selected from the group consisting of O, S, and NR$^5$, wherein R$^5$ is H or (C1-C6)alkyl, the alkyl being optionally substituted with hydroxyl or with N(R$^6$)$_2$ on any carbon atom thereof other than a carbon atom bonded directed to the nitrogen atom of NR$^5$, wherein the heterocyclyl ring is further optionally mono- or independently multi-substituted with (C1-C6)alkyl, the alkyl being optionally substituted with hydroxyl or with N(R$^6$)$_2$, wherein each R$^6$ is independently H or (C1-C6)alkyl;

X, Y and Z are independently hydrogen, fluoro, chloro, methoxy, CN, NO$_2$, CF$_3$, NHCOR, lower alkyl, C(R$^3$R$^4$) NR$^3$R$^4$, C(R$^3$R$^4$)$_2$OH, C(R$^3$R$^4$)$_2$OR, CO$_2$R, CONR$_2$;

or a pharmaceutically acceptable salt thereof.

For example, R$^2$ can be a group of formula

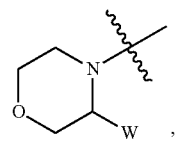

wherein W is H or (C1-C6)alkyl, wherein the alkyl is optionally further substituted with hydroxyl or N(R$^7$)$_2$, wherein each R$^7$ is independently H or (C1-C6)alkyl or where N(R$^7$)$_2$ is a 5-, 6-, or 7-membered heterocyclyl ring, wherein a wavy line indicates a position of bonding.

In various embodiments of formula (I) throughout, R$^1$ can be a 5-membered heteroaryl ring comprising 1, 2, 3, or 4 heteroatoms comprising independently selected N, NR', O, or S, bonded via a carbon atom to the N(9) adenine ring nitrogen atom bearing group R$^1$, wherein any carbon atom other than the bonded carbon atom is substituted with R';

R' can be H, (C1-C4)alkyl, or (C1-C4)alkyl substituted with F, OH, or OR.

More specifically, R$^1$ can be a 5-membered heteroaryl ring comprising 2 heteroatoms, such as for the following compounds:

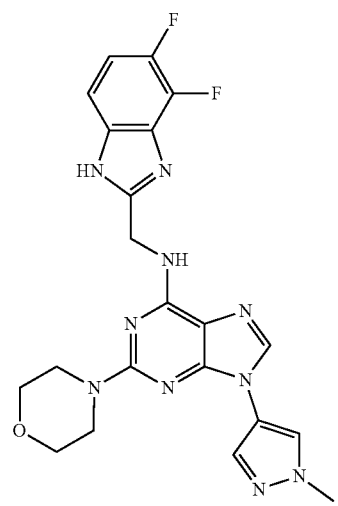

Compound 1

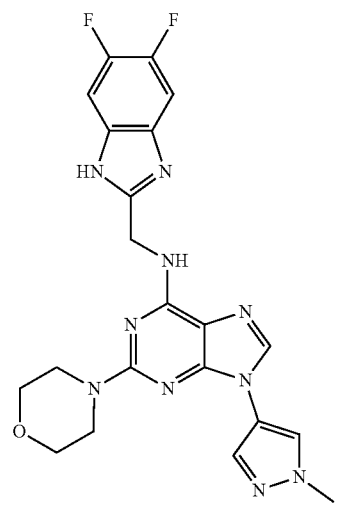

Compound 2

Compound 3
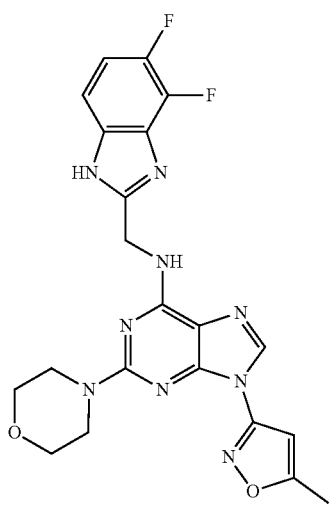
Compound 4
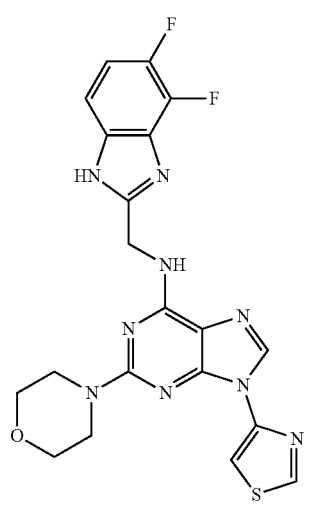
Compound 5
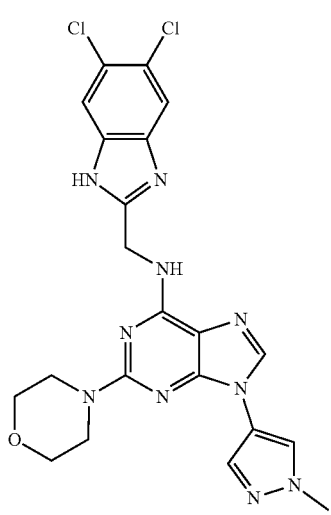
Compound 6
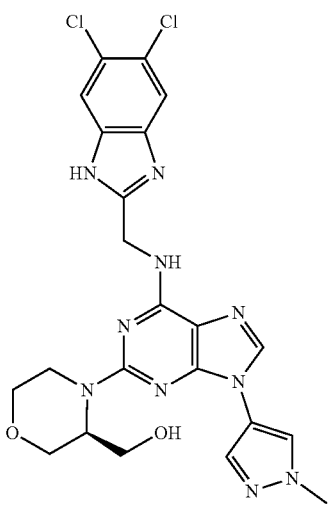
Compound 7
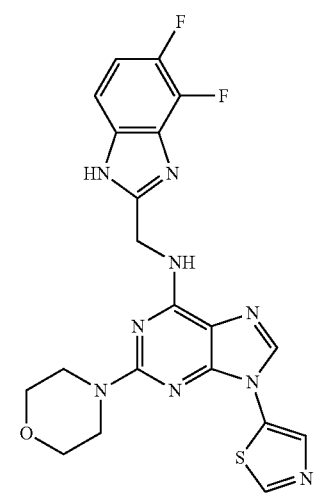
Compound 8

-continued

Compound 9

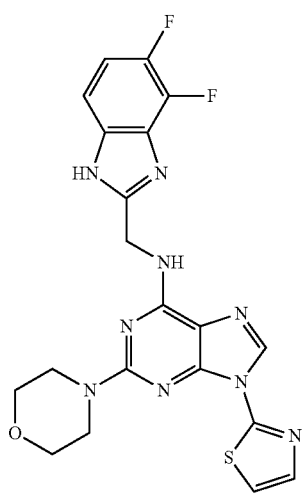

Compound 10

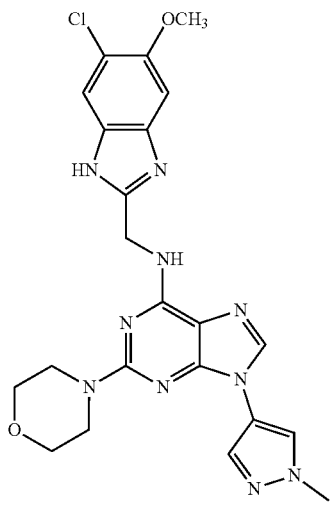

Compound 11

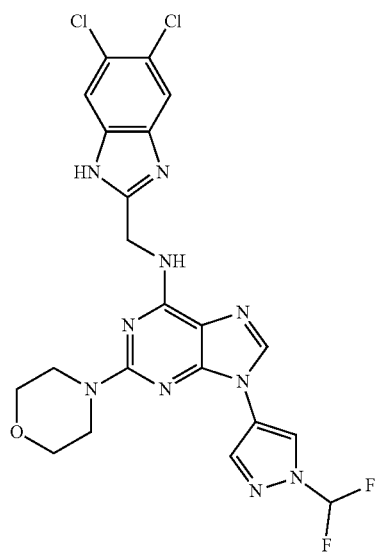

In various embodiments, group $R^1$ in the compound of formula (I) can be any one of

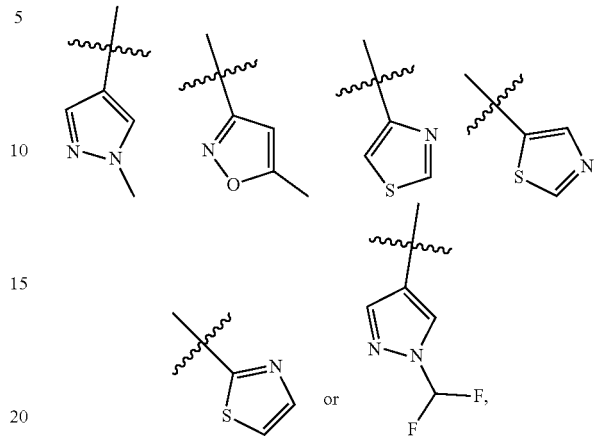

wherein a wavy line indicates a position of bonding.

In various embodiments, the cyclin-dependent kinase is cyclin-dependent kinase 12 or 13 (CDK12 or CDK13).

In various embodiments, the compound of formula (I) is a highly selective inhibitor of the CDK kinases, having much lower activity versus certain other kinase enzymes, for example, wherein the compound of formula (I) is not an effective inhibitor of casein kinase 1δ or 1ε (CK1δ/ε).

In various embodiments, the CDK that is inhibited by practice of a method of the invention is disposed within the body tissue of a patient afflicted with cancer.

Accordingly, the invention further provides, in various embodiments, a method of treating a cancer in a patient afflicted therewith, comprising administering to the patient an effective dose of a compound of formula (I)

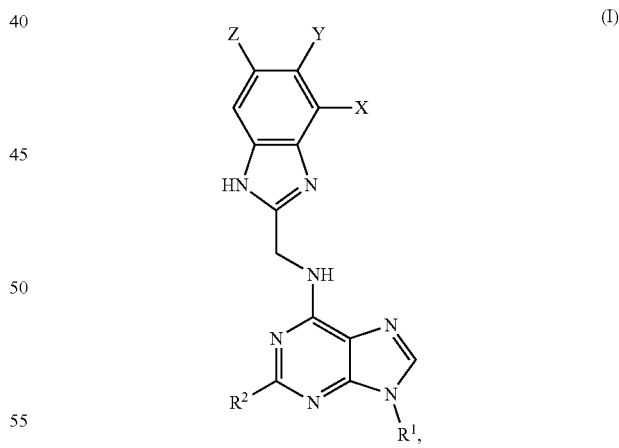

(I)

wherein
$R^1$ is aryl or heteroaryl optionally mono- or independently multi-substituted with J;
wherein J independently at each occurrence is selected from the group consisting of F, Cl, Br, I, OR, CN, $CF_3$, $OCF_3$, $NO_2$, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, N(R)N(R)CON(R$_2$), N(R)SO$_2$R, N(R)SO$_2$N(R)$_2$, N(R)C(O) OR, N(R)C(O)R, N(R)C(S)R, N(R)C(O)N(R)$_2$, N(R)C(S)N (R)$_2$, N(COR)COR, N(OR)R, C(=NH)N(R$_2$), C(O)N(OR) R, C(=NOR)R, (C$_{1-4}$)alkyl, (C$_{1-4}$)alkoxy, (C$_{1-4}$)acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with R, (C$_{1-6}$)alkyl, (C$_{2-6}$)alkenyl, (C$_{2-6}$)alkynyl, (C$_{1-6}$)haloalkyl, (C$_{1-6}$)alkoxy, (C$_{1-6}$)haloalkoxy, cycloalkyl(C$_{0-6}$)alkyl, heterocyclyl(C$_{0-6}$)alkyl, aryl(C$_{0-6}$)alkyl, or heteroaryl (C$_{0-6}$)alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a (C$_{3-8}$)heterocyclyl mono- or multi-substituted with R; optionally further comprising 1-3 additional heteroatoms selected from the group consisting of O, N, S, S(O) and S(O)$_2$;

wherein R is independently at each occurrence is selected from the group consisting of hydrogen, deuterium, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 J$^R$; or wherein two R groups together with a nitrogen atom or with two adjacent nitrogen atoms to which they are bonded can together form a (C$_{3-8}$)heterocyclyl substituted with 0-3 J$^R$; optionally further comprising 1-3 additional heteroatoms selected from the group consisting of O, N, S, S(O) and S(O)$_2$;

wherein any cycloalkyl, aryl, heterocyclyl, or heteroaryl can be fused, bridged, or in a spiro configuration with one or more additional optionally mono- or independently multi-substituted cycloalkyl, aryl, heterocyclyl, and heteroaryl, monocyclic, bicyclic, bicyclic or polycyclic, saturated, partially unsaturated, or aromatic rings;

R$^2$ is NR$^3$R$^4$, wherein R$^3$ and R$^4$ are each independently H or (C1-C6)alkyl, the alkyl being optionally substituted with hydroxyl or with N(R$^6$)$_2$ on any carbon atom thereof other than a carbon atom bonded directed to the nitrogen atom of NR$^3$R$^4$, or R$^3$ and R$^4$ together with the nitrogen atom to which they are bonded form a 5- to 7-membered heterocyclyl ring optionally comprising 1 or 2 additional heteroatoms selected from the group consisting of O, S, and NR$^5$, wherein R$^5$ is H or (C1-C6)alkyl, the alkyl being optionally substituted with hydroxyl or with N(R$^6$)$_2$ on any carbon atom thereof other than a carbon atom bonded directed to the nitrogen atom of NR$^5$, wherein the heterocyclyl ring is further optionally mono- or independently multi-substituted with (C1-C6)alkyl, the alkyl being optionally substituted with hydroxyl or with N(R$^6$)$_2$, wherein each R$^6$ is independently H or (C1-C6)alkyl;

X, Y and Z are independently hydrogen, fluoro, chloro, methoxy, CN, NO$_2$, CF$_3$, NHCOR, lower alkyl, C(R')$_2$NR$_2$, C(R')$_2$OH, C(R')$_2$OR, CO$_2$R, CONR$_2$;

or a pharmaceutically acceptable salt thereof.

For example, R$^2$ can be a group of formula

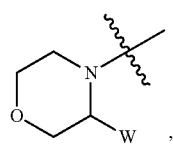

wherein W is H or (C1-C6)alkyl, wherein the alkyl is optionally further substituted with hydroxyl or N(R$^7$)$_2$, wherein each R$^7$ is independently H or (C1-C6)alkyl or where N(R$^7$)$_2$ is a 5-, 6-, or 7-membered heterocyclyl ring, wherein a wavy line indicates a position of bonding.

For example, in various embodiments, R$^1$ is a 5-membered heteroaryl ring comprising 1, 2, 3, or 4 heteroatoms comprising independently selected N, NR', O, or S, bonded via a carbon atom to the N(9) adenine ring nitrogen atom bearing group R$^1$, wherein any carbon atom other than the bonded carbon atom is substituted with R';

R' is H or (C1-C4)alkyl. More specifically, R$^1$ is a 5-membered heteroaryl ring comprising 2 heteroatoms, such as compound 5.

For example, the cancer being treated can be breast cancer, brain cancer or ovarian cancer.

The invention further provides, in various embodiments, a compound of formula (I)

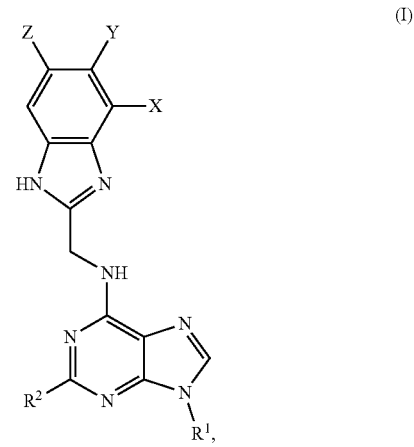

(I)

wherein

R$^1$ is aryl or heteroaryl optionally mono- or independently multi-substituted with J;

wherein J independently at each occurrence is selected from the group consisting of F, Cl, Br, I, OR, CN, CF$_3$, OCF$_3$, NO$_2$, O, S, C(O), C(S), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-4}$NHC(O)R, N(R)N(R)C(O)R, N(R)N(R)C(O)OR, N(R)N(R)CON(R$_2$), N(R)SO$_2$R, N(R)SO$_2$N(R)$_2$, N(R)C(O) OR, N(R)C(O)R, N(R)C(S)R, N(R)C(O)N(R)$_2$, N(R)C(S)N (R)$_2$, N(COR)COR, N(OR)R, C(=NH)N(R$_2$), C(O)N(OR) R, C(=NOR)R, (C$_{1-4}$)alkyl, (C$_{1-4}$)alkoxy, (C$_{1-4}$)acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with R, (C$_{1-6}$)alkyl, (C$_{2-6}$)alkenyl, (C$_{2-6}$)alkynyl, (C$_{1-6}$)haloalkyl, (C$_{1-6}$)alkoxy, (C$_{1-6}$)haloalkoxy, cycloalkyl(C$_{0-6}$)alkyl, heterocyclyl(C$_{0-6}$)alkyl, aryl(C$_{0-6}$)alkyl, or heteroaryl (C$_{0-6}$)alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a (C$_{3-8}$)heterocyclyl mono- or multi-substituted with R; optionally further comprising 1-3 additional heteroatoms selected from the group consisting of O, N, S, S(O) and S(O)$_2$;

wherein R is independently at each occurrence is selected from the group consisting of hydrogen, deuterium, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 $J^R$; or wherein two R groups together with a nitrogen atom or with two adjacent nitrogen atoms to which they are bonded can together form a $(C_{3-8})$heterocyclyl substituted with 0-3 $J^R$; optionally further comprising 1-3 additional heteroatoms selected from the group consisting of O, N, S, S(O) and S(O)$_2$;

wherein any cycloalkyl, aryl, heterocyclyl, or heteroaryl can be fused, bridged, or in a spiro configuration with one or more additional optionally mono- or independently multi-substituted cycloalkyl, aryl, heterocyclyl, and heteroaryl, monocyclic, bicyclic, bicyclic or polycyclic, saturated, partially unsaturated, or aromatic rings;

$R^2$ is $NR^3R^4$, wherein $R^3$ and $R^4$ are each independently H or (C1-C6)alkyl, the alkyl being optionally substituted with hydroxyl or with $N(R^6)_2$ on any carbon atom thereof other than a carbon atom bonded directed to the nitrogen atom of $NR^3R^4$, or $R^3$ and $R^4$ together with the nitrogen atom to which they are bonded form a 5- to 7-membered heterocyclyl ring optionally comprising 1 or 2 additional heteroatoms selected from the group consisting of O, S, and $NR^5$, wherein $R^5$ is H or (C1-C6)alkyl, the alkyl being optionally substituted with hydroxyl or with $N(R^6)_2$ on any carbon atom thereof other than a carbon atom bonded directed to the nitrogen atom of $NR^5$, wherein the heterocyclyl ring is further optionally mono- or independently multi-substituted with (C1-C6)alkyl, the alkyl being optionally substituted with hydroxyl or with $N(R^6)_2$, wherein each $R^6$ is independently H or (C1-C6)alkyl;

X, Y and Z are independently hydrogen, fluoro, chloro, methoxy, CN, NO$_2$, CF$_3$, NHCOR, lower alkyl, C(R')$_2$NR$_2$, C(R')$_2$OH, C(R')$_2$OR, CO$_2$R, CONR$_2$;

or a pharmaceutically acceptable salt thereof.

For example, $R^2$ can be a group of formula

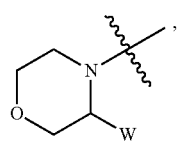

wherein W is H or (C1-C6)alkyl, wherein the alkyl is optionally further substituted with hydroxyl or $N(R^7)_2$, wherein each $R^7$ is independently H or (C1-C6)alkyl or where $N(R^7)_2$ is a 5-, 6-, or 7-membered heterocyclyl ring, wherein a wavy line indicates a position of bonding.

More specifically, in various embodiments, $R^1$ is a 5-membered heteroaryl ring comprising 2 heteroatoms. For example, the compound can be any one of the following compounds:

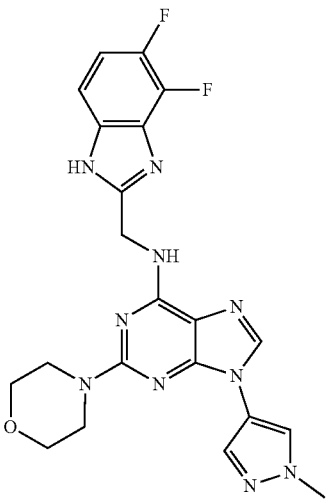

Compound 1

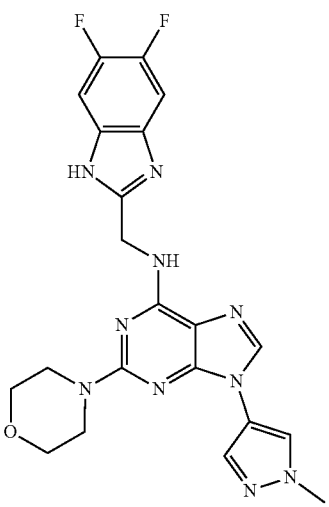

Compound 2

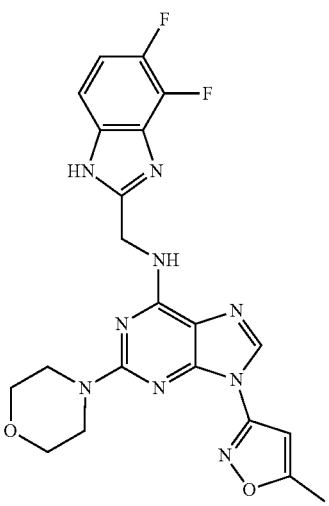

Compound 3

Compound 4
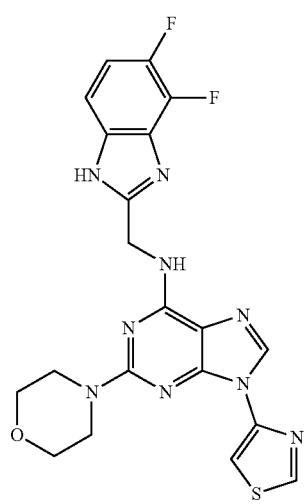
Compound 5
Compound 6
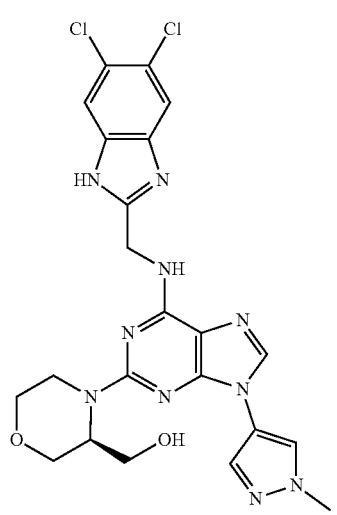
Compound 7
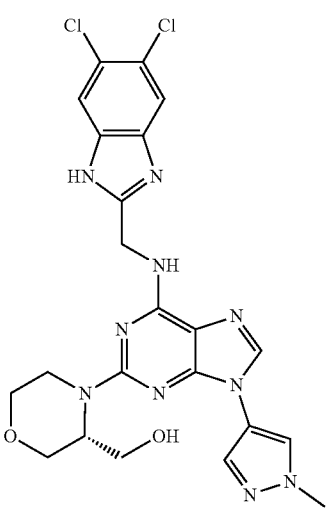
Compound 8
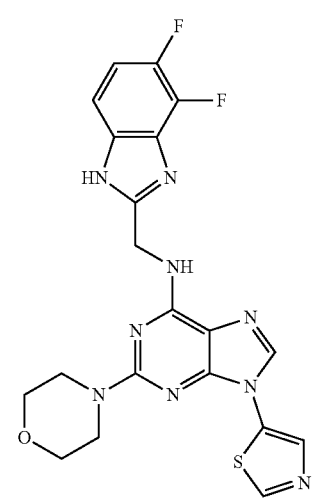
Compound 9
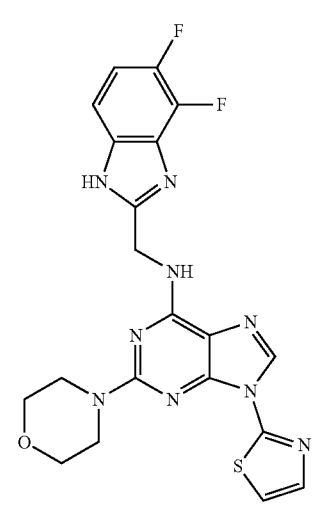

Compound 10

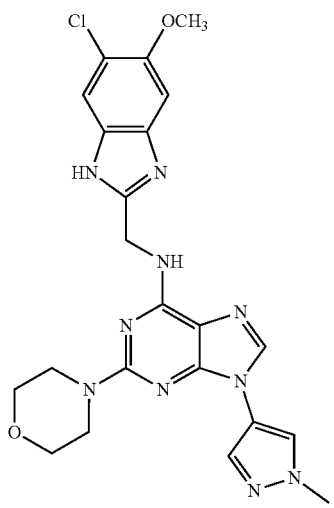

Compound 11

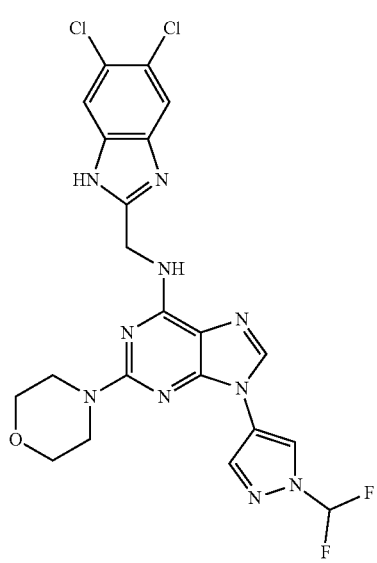

These compounds of formula (I), such as Compounds 1-9 (see structures above, and bioactivity data in Table 1, below), while having at best only moderate bioactivity for inhibition of casein kinase 1 b (CK1δ) and casein kinase 1ε (CK1ε), i.e., typically 1 μM and higher $IC_{50}$ values versus these targets, exhibit unexpectedly favorable properties in terms of highly potent inhibition of cyclin-dependent kinase 12 (CDK12) and cyclin-dependent kinase 13 (CDK13), showing potencies of $IC_{50}$ value in the single or double digit nM concentration range, for the most part.

Formula (I) encompasses both benzimidazole tautomers of the depicted formulas, although only one is depicted for clarity.

The compounds of formula (I), including for practice of methods of the invention, include the following compounds:

Compound 1

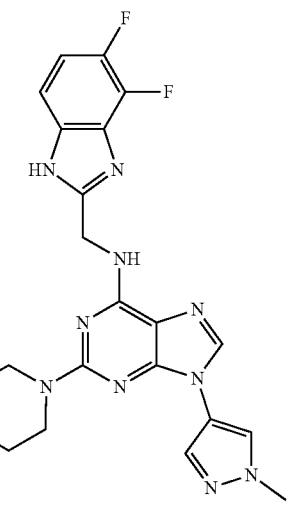

Compound 2

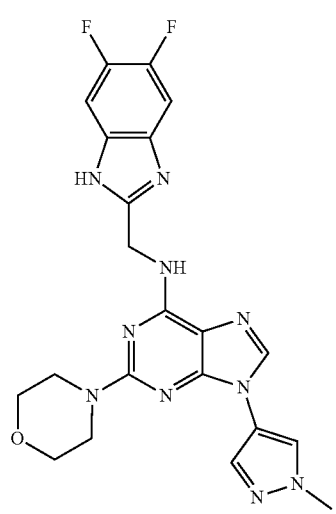

Compound 3

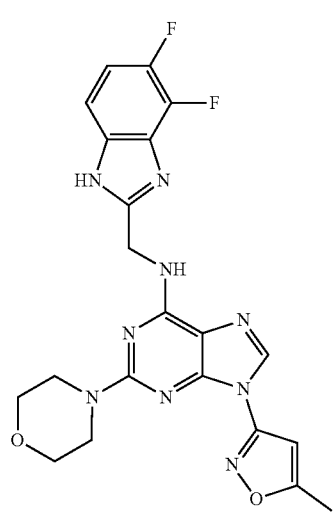

Compound 4
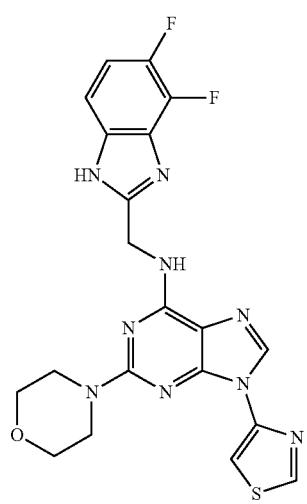
Compound 5
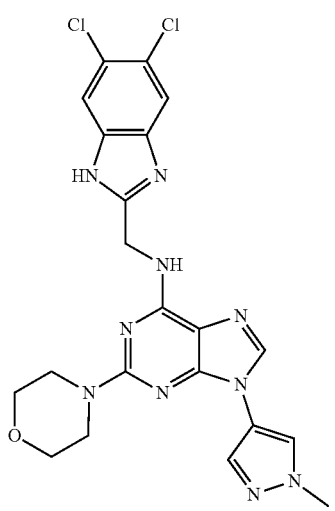
Compound 6
Compound 7
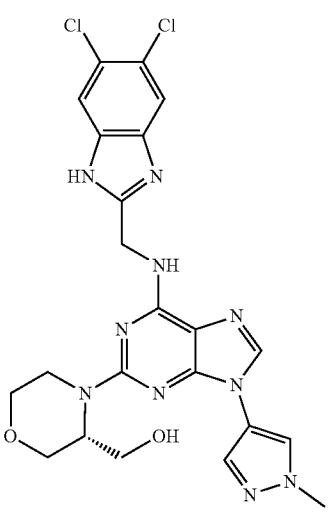
Compound 8
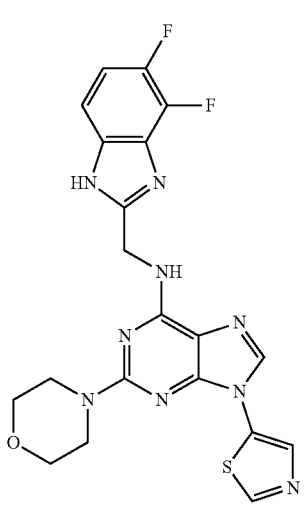
Compound 9
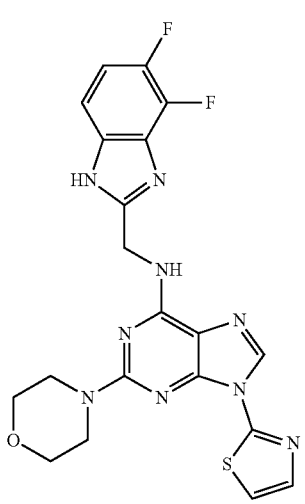

-continued

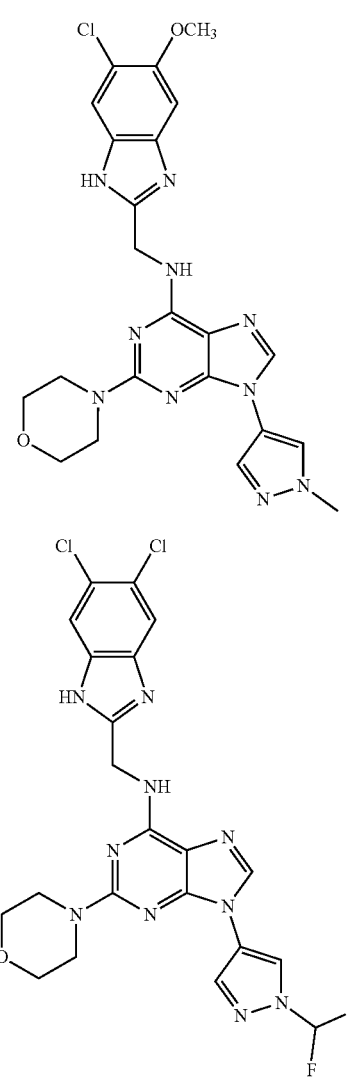

Compound 10

Compound 11

BRIEF DESCRIPTION OF THE FIGURES

FIGS. 2a and 2b. Selectivity of selected CDK12/13 inhibitors against other CDKs (% of inhibition at 10 μM)

DETAILED DESCRIPTION

Figure 1:
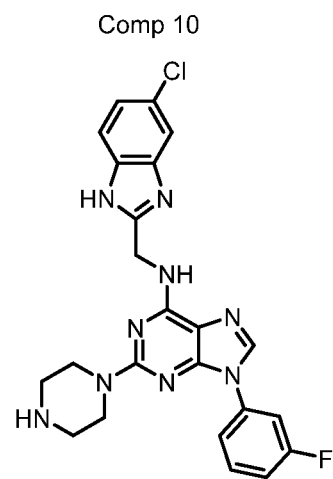
FIG. 1. Structure and biological activity of compound 10

The invention summarized here started with studies of kinase inhibitors from a program targeting casein kinases 1δ and E (CK1δ/ε). One of the initial hits generated in the CK1δ/εprogram, compound 10 (FIG. 1), while being a single-digit nM inhibitor of CK1δ, was discovered to inhibit several kinases in the CDK family when tested at 10 μM concentration (CDK4/Cyc1—99.8% inh, CDK7—98.5% inh, CDK13—12% of inhibition). Further modification of this series, particularly by introducing certain heteroaromatic groups at purine N9 position, led to compounds that have <50 nM $IC_{50}$ as CDK12/13 inhibitors with very weak activity against CK1δ/ε(typically >1 μM, Table 1).

Figure 3:
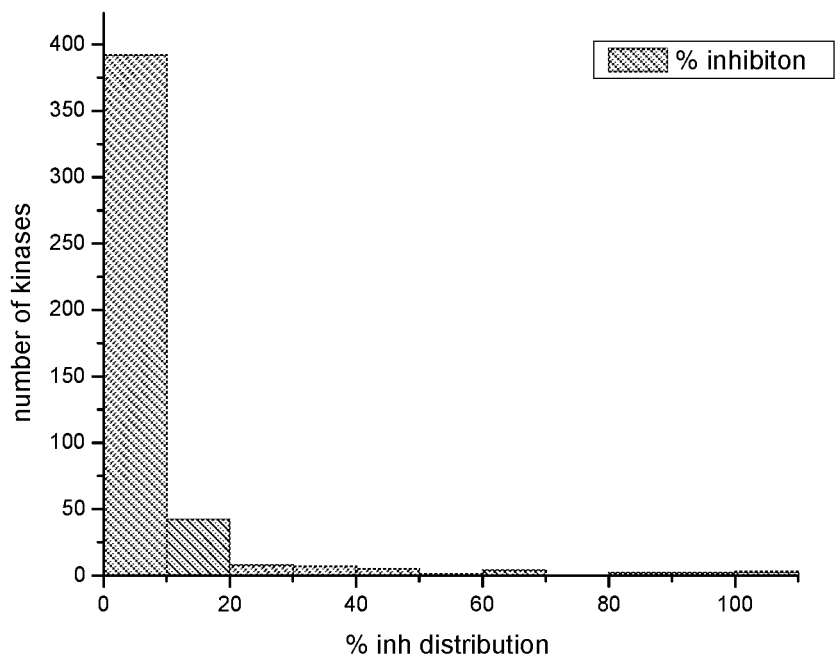
FIG. 3. Selectivity of compound 5 (inhibition at 10 μM) against panel of 465 kinases FIG. 4. Plasma concentration versus time profile for compound 5 (points are the average of 3 mice) following IV/PO administration at dose of 1/20 mg/kg using 10/10/80 DMSO/Tween 80/water.

These compounds showed excellent potency in cell proliferation assays (MDA-MB-231, U87 cell lines, $EC_{50}$<100 nM). Selected CDK12/13 inhibitors showed good selectivity in CDK panel tested (compound 1, 3 and SR-3029, FIG. 2). Additionally, one of the frontrunner compounds compound 5 is remarkably selective against panel of other 465 kinases tested (FIG. 3).

Table 1, below, shows SAR data for CDK12/13 selective inhibitors of formula

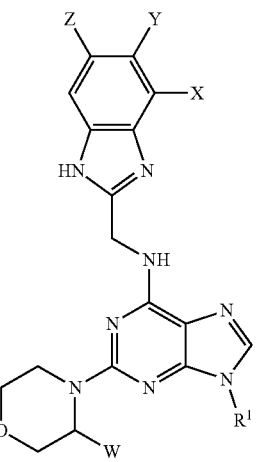

wherein the substituents W, X, Y, Z, and $R^1$, are as specified in the respective Table columns. Footnotes are as follows:

[a] CK1d/e inhibition data determined from an in-house kinase inhibition assay.

[b] Competition binding assays, DiscoverX.

[c] Cell assay results for inhibition of Ser2 in MDA-MB-231 cell line.

[d] Growth inhibition in U87 and MDA-MB-231 cell lines, 72 h.

TABLE 1
SAR data for CDK12/13 selective inhibitors
| ID | R | Z | Y | X | W | CK1σ IC$_{50}$ [nM]$^a$ | CK1ε IC$_{50}$ [nM]$^a$ | CDK12 K$_d$ [nM]$^b$ | CDK13 K$_d$ [nM]$^b$ | pSer2 IC$_{50}$ [nM]$^c$ | U87 GI$_{50}$ [nM]$^d$ | MDA-MB-231 GI$_{50}$ [nM]$^d$ |
|---|---|---|---|---|---|---|---|---|---|---|---|---|
| 1 | 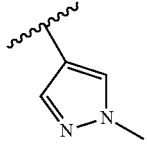 [SMILES: *c1cnn(C)c1] | H | F | F | H | 8600 | 4600 | 14 | 5 | 840 | 105 | 62 |
| 2 | 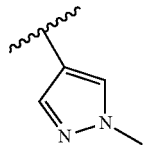 [SMILES: *c1cnn(C)c1] | F | F | H | H | >9900 | 6500 | —$^e$ | —$^e$ | 2200 | 95 | 66 |
| 3 | 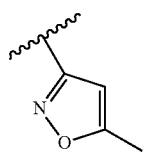 [SMILES: *c1cc(C)on1] | H | F | F | H | 4745 | 1250 | 22 | 4 | 375 | 13 | 6 |
| 4 | 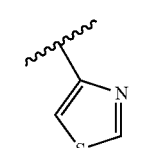 | H | F | F | H | 870 | 1279 | 18 | 6 | 215 | <2 | <2 |
| 5 | 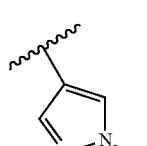 | Cl | Cl | H | H | 2935 | 1580 | 630 | 5 | 95 | <2 | <2 |
| 6 | 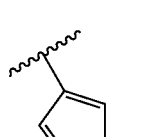 | Cl | Cl | H | S-CH$_2$OH | 333 | 145 | —$^e$ | —$^e$ | 162 | 51 | 19 |
| 7 | 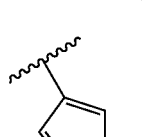 | Cl | Cl | H | R-CH$_2$OH | 6065 | 5355 | —$^e$ | —$^e$ | 253 | 78 | 51 |
| 8 | 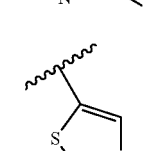 | H | F | F | H | 419 | 632 | —$^e$ | —$^e$ | 158 | 7 | 17 |
| 9 | 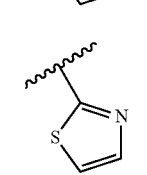 | H | F | F | H | 400 | 1070 | —$^e$ | —$^e$ | 463 | 24 | 77 |

TABLE 1-continued

SAR data for CDK12/13 selective inhibitors

| ID | R | Z | Y | X | W | CK1σ IC$_{50}$ [nM]$^a$ | CK1ε IC$_{50}$ [nM]$^a$ | CDK12 K$_d$ [nM]$^b$ | CDK13 K$_d$ [nM]$^b$ | pSer2 IC$_{50}$ [nM]$^c$ | U87 GI$_{50}$ [nM]$^d$ | MDA-MB-231 GI$_{50}$ [nM]$^d$ |
|---|---|---|---|---|---|---|---|---|---|---|---|---|
| 10 | (pyrazole-CH$_3$) | Cl | OCH$_3$ | H | H | 7729 | 2617 | 38 | 2 | — | 147 | 134 |
| 11 | (pyrazole-CHF$_2$) | Cl | Cl | H | H | 1257 | 709 | 310 | 9 | — | 7 | 11 |

$^a$CK1d/e inhibition data determined from an in-house kinase inhibition assay.
$^b$Competition binding assays, DiscoverX.
$^c$Cell assay results for inhibition of Ser2 in MDA-MB-232 cell line.
$^d$Growth inhibition in U87 and MDA-MB-232 cell lines, 72 h.
$^e$Submitted for testing

TABLE 2

ADME data for CDK12/13 selective inhibitors

| Compound | Solubility (μm)$^a$ | Microsome stability t$_{1/2}$ min (HMR)$^b$ | CYP inhibition, % inh$^c$ | | | |
|---|---|---|---|---|---|---|
| | | | 1A2 | 2C9 | 2D6 | 3A4 |
| 1 | 6.1 | 22/9/20 | 10 | 23 | −3 | 56 |
| 2 | 0.8 | 39/11/18 | 5 | 23 | 2 | 55 |
| 3 | 3.6 | 13/7/11 | 5 | 23 | 2 | 55 |
| 4 | 0.8 | 16/6/9 | 97 | 89 | 57 | 89 |
| 5 | 0.3 | 19/12/16 | 50 | 70 | 66 | 89 |
| 6 | 0.8 | 21/13/19 | 42 | 69 | 42 | 77 |
| 7 | 0.7 | 27/18/25 | 39 | 54 | 29 | 54 |

$^a$Solubility in pH 7.4 phosphate buffered saline.
$^b$Microsome stability using human, mouse and rat liver microsomes, with sunitinib as the reference (75/13/28), half-life, minutes.
$^c$Cytochrome P450 inhibition assay, % inhibition

TABLE 3

Mouse PK data for selected CDK12/13 inhibitors

| Compound | Route/dose$^2$ | T$_{1/2}$ hr | T$_{max}$ hr | C$_{max}$ ng/mL | C$_{max}$ μM | AUC$_{last}$ min*ng/mL | AUC$_{last}$ μM.hr | AUC$_{INF\_dos}$ min*ng/mL | AUC % Extrap | CL_obs mL/min/kg | F % |
|---|---|---|---|---|---|---|---|---|---|---|---|
| 1 | IP 30 | 2.98 | 1.00 | 9330.0 | 20.0 | 1526112 | 55 | 1528396 | 0.1 | 13.4 | |
| 5 | IP 20 | 4.83 | 1.33 | 6816.7 | 13.6 | 2426860 | 81 | 2499284 | 3.1 | 8.3 | |
| 5 | PO 20 | 3.95 | 2.67 | 1301 | 2.61 | 697216 | 23 | 707526 | 1.7 | 29.5 | 29.7 |
| 7 | IP 20 | 3.71 | 1.00 | 1430 | 2.70 | 328306 | 10 | 331817 | 1.0 | 61.6 | |

Figure 4:
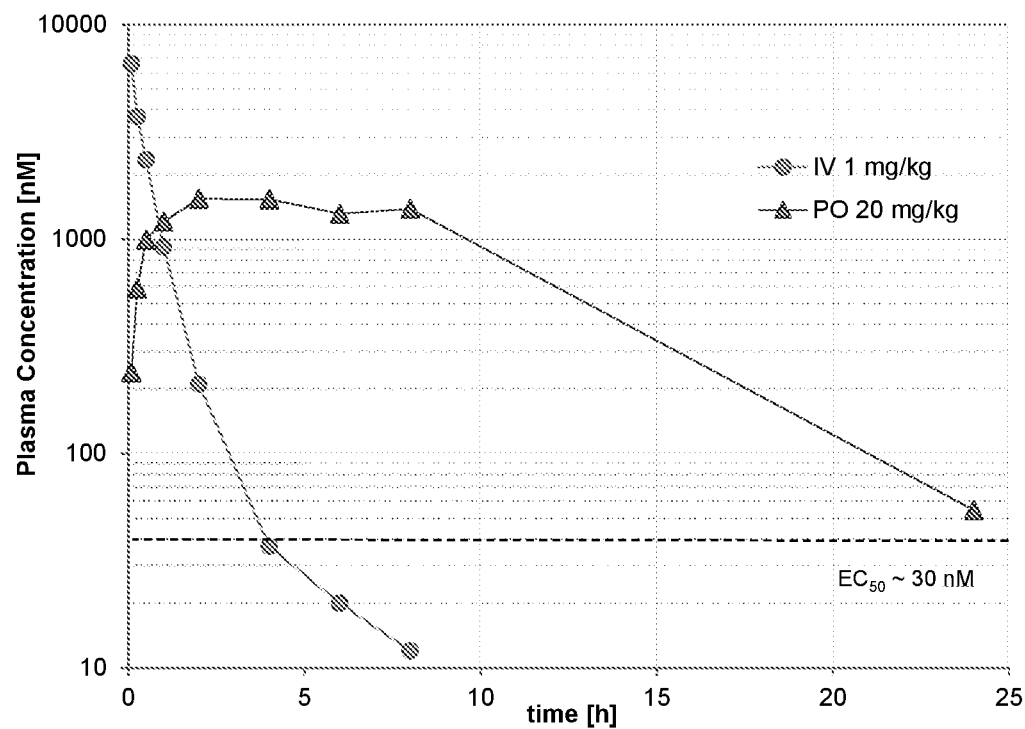

$^a$mg/kg, formulation in 10/10/80 DMSO/Tween-80/water;

FIG. 4, below, shows plasma concentration versus time profile for compound 5 (points are the average of 3 mice) following IV/PO administration at dose of 1/20 mg/kg using 10/10/80 DMSO/Tween 80/water.

Figure 5:
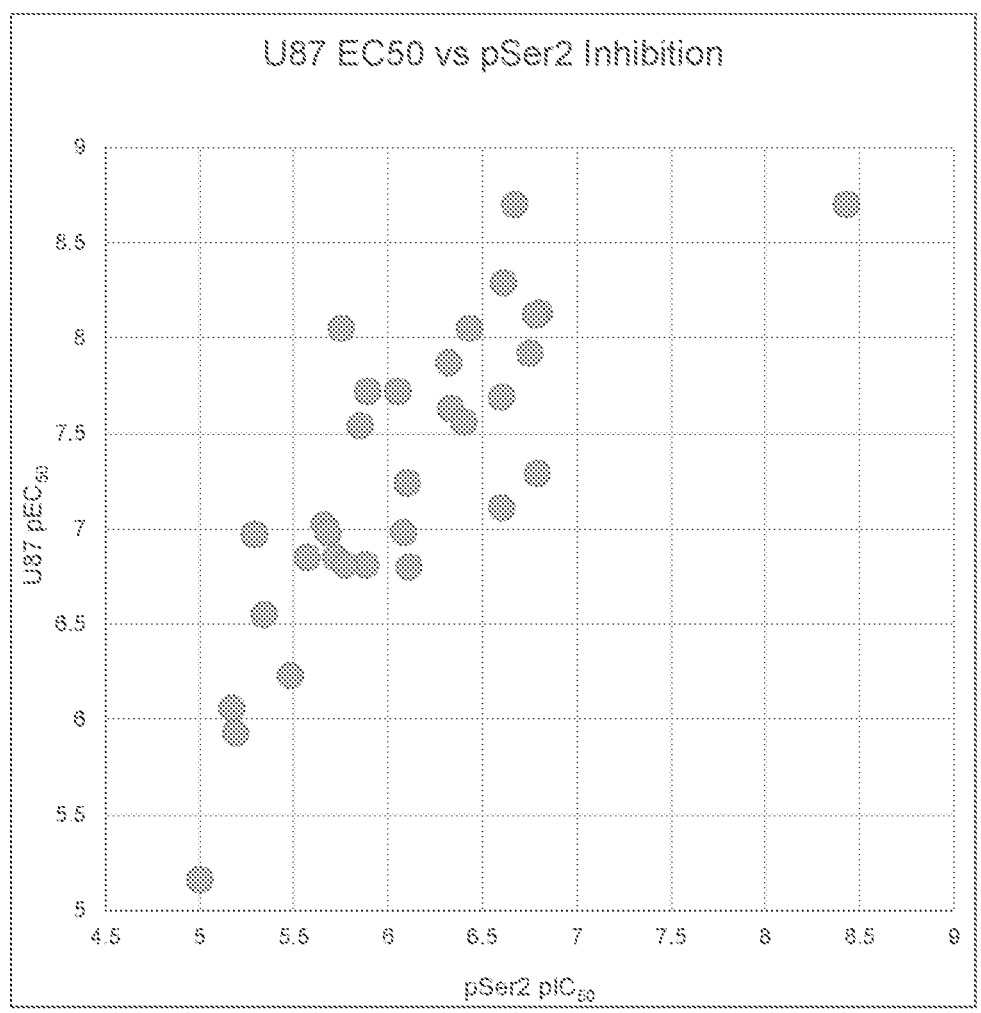
FIG. 5. Correlation plot of U87 growth inhibition vs inhibition of Ser2 phosphorylation FIG. 6. Correlation plot of MDA-MB-231 growth inhibition vs inhibition of Ser2 phosphorylation FIG. 7. MDA-MB-231 cell proliferation assay used to calculate synergy index (CI) of Cisplatin, Olaparib and Irinotecan+compound 5 calculated using CompuSyn.
Figure 6:
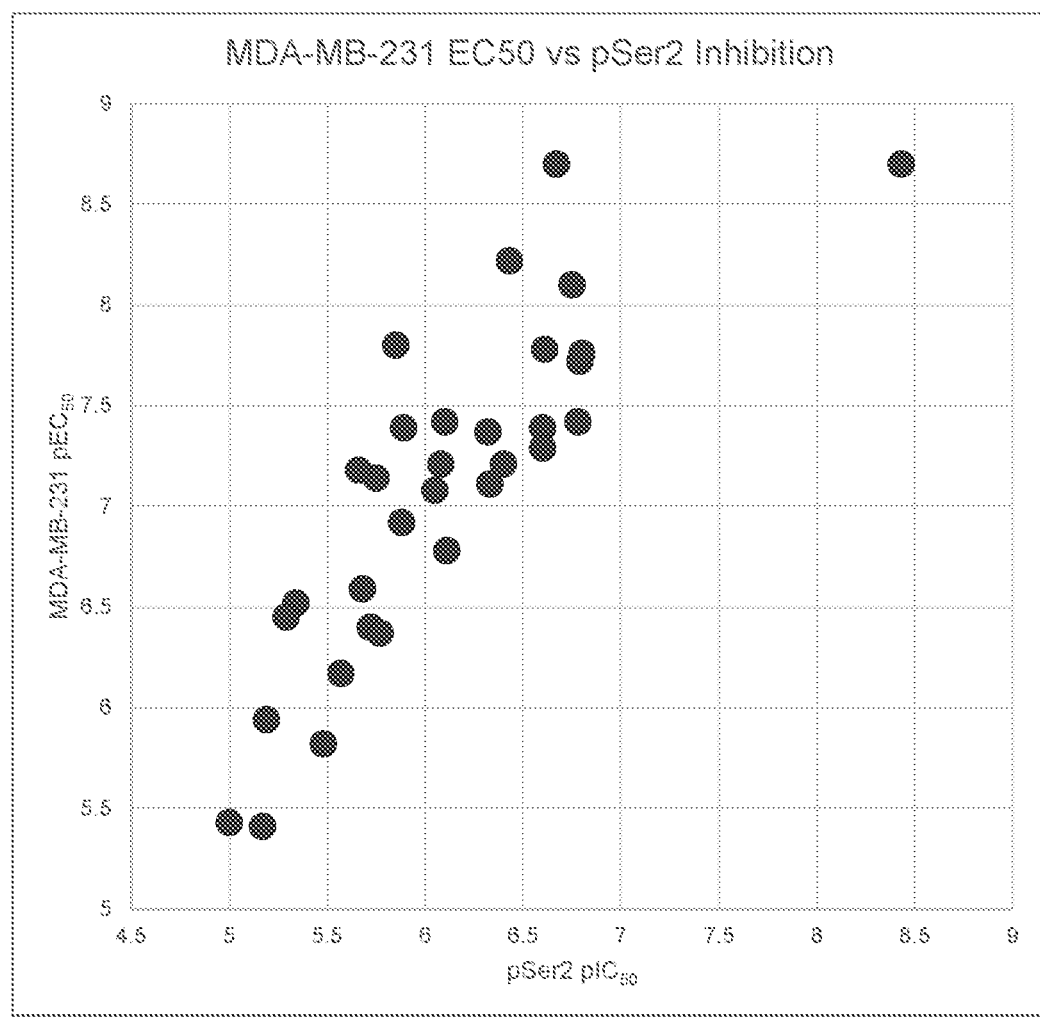
Figure 7:
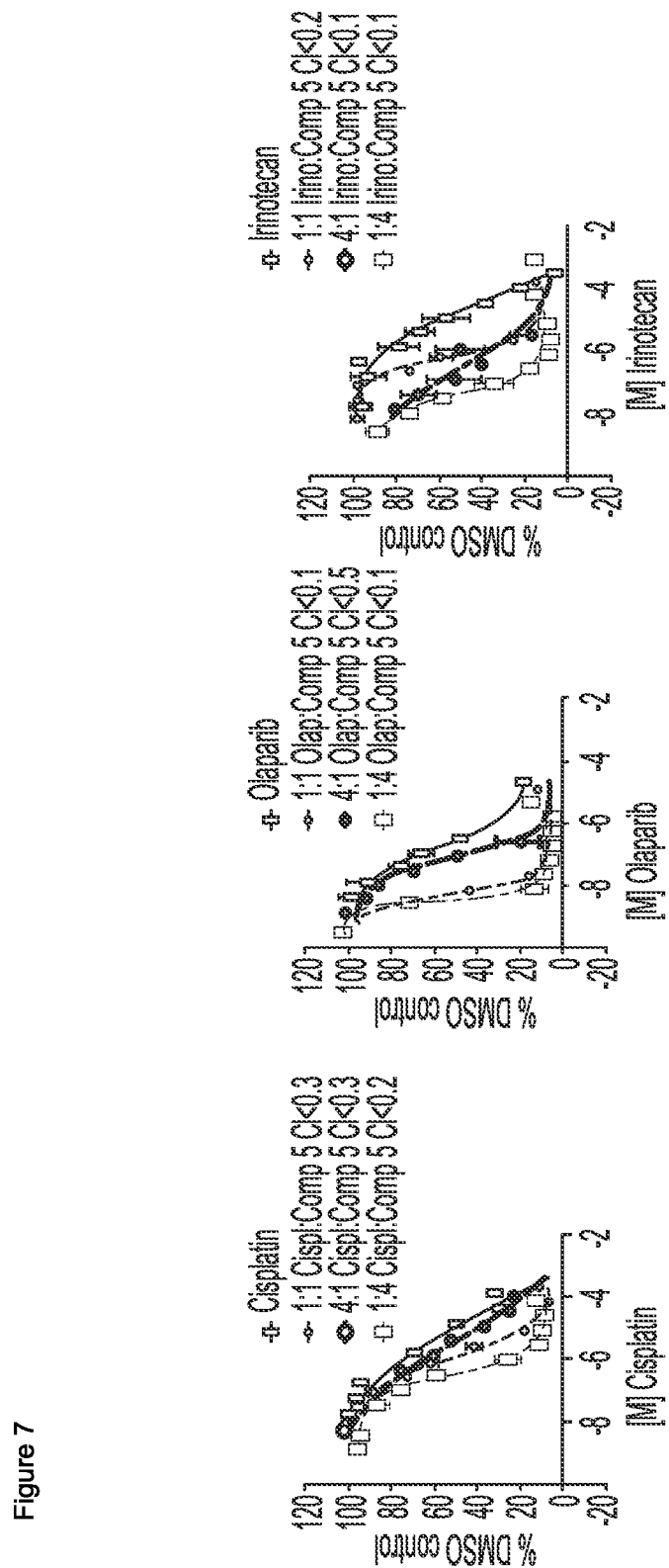

In addition to screening a selected set of new inhibitors in CDK12/13 enzyme assays using Kinomescan™ technology, we tested all new compounds in a mechanism of action assay, which detects inhibition of phosphorylation of serine 2 (pSer2) on the C-terminal repeat domain (CTD) of RNA pol II. CDK12 and CDK13 (in association with cyclin K), as members of larger class of transcription-regulating kinases, phosphorylate the CTD of RNA pol II at Ser2 position in particular.[1] Thus we examined if CDK12/13 inhibitors also inhibited Ser2 phosphorylation in cells; these data are provided in the "pSer2" column of the SAR table. In order to confirm that CDK12/13 inhibition is driving cell death, we also plotted the growth inhibition pIC$_{50}$'s with pSer2 inhibition data. There was a good correlation when using the cell proliferation data from both U87 and MDA-MB-231 cell lines (FIGS. 5 and 6).

Multimodal use of chemotherapy remains ineffective in metastatic Her2+ and triple negative breast cancers (TNBC). In TNBC, targeted therapies in addition to Olaparib are desperately needed and determination of combination treatments need to be established. Because it is known that CDK12 and CDK13 control expression of genes involved in DNA damage repair, we examined whether inhibition of CDK12/13 augmented the killing effect of a select set of TNBC clinical agents. We applied the method of Chou and Talalay, calculating the EC$_H$, ratios of the observed growth inhibition following treatment with compound 5 plus Cisplatin, Olaparib and Irinotecan relative to individual treatment to determine a combination index (CI), calculated using CompuSyn.[1] The CI offers a quantitative measure to determine if a combination of agents acts in synergy (CI<1), additively (CI=1), or is antagonistic (CI>1). Importantly, cell proliferation studies demonstrated that compound 5 acted synergistically with Cisplatin with a CI of <0.3 and was highly synergistic with Olaparib and irinotecan (FIG.

Figure 8:
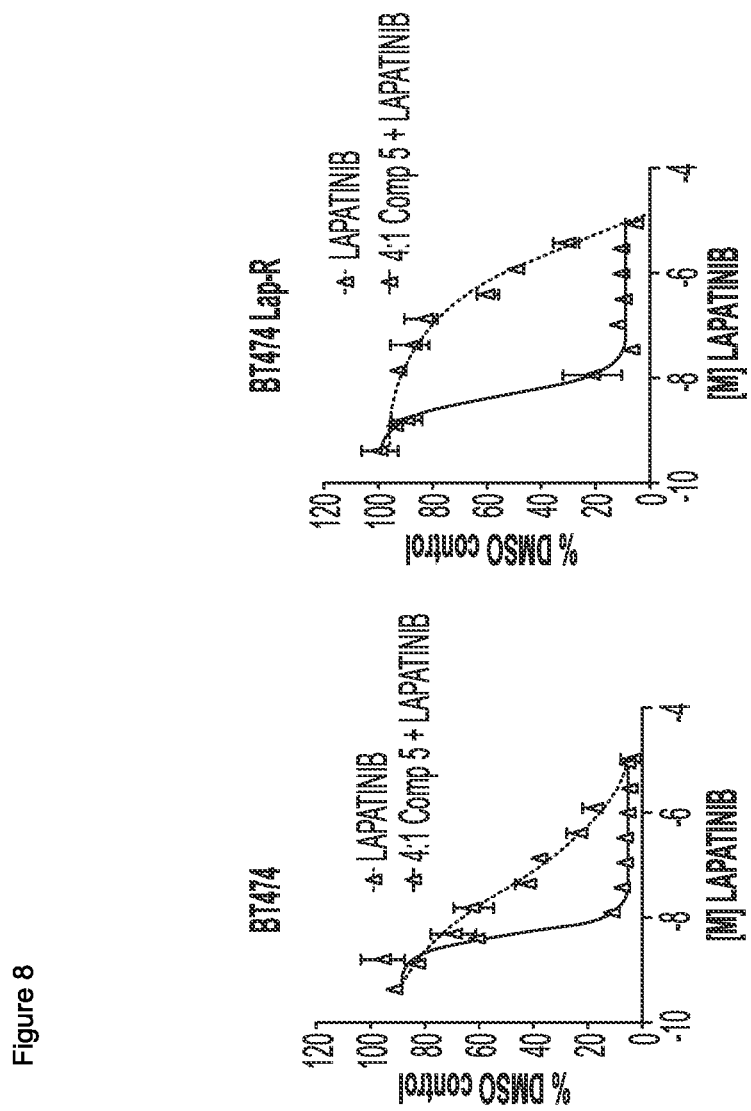
FIG. 8. Cell proliferation assay used to calculate synergy index (CI) of lapatinib+compound 5 calculated using CompuSyn.

7). In Her2+ breast cancers compound 5 was highly synergistic with lapatinib and trastuzumab in certain anti-Her2+ sensitive and resistant cell lines (FIG. 8).

Figure 9:
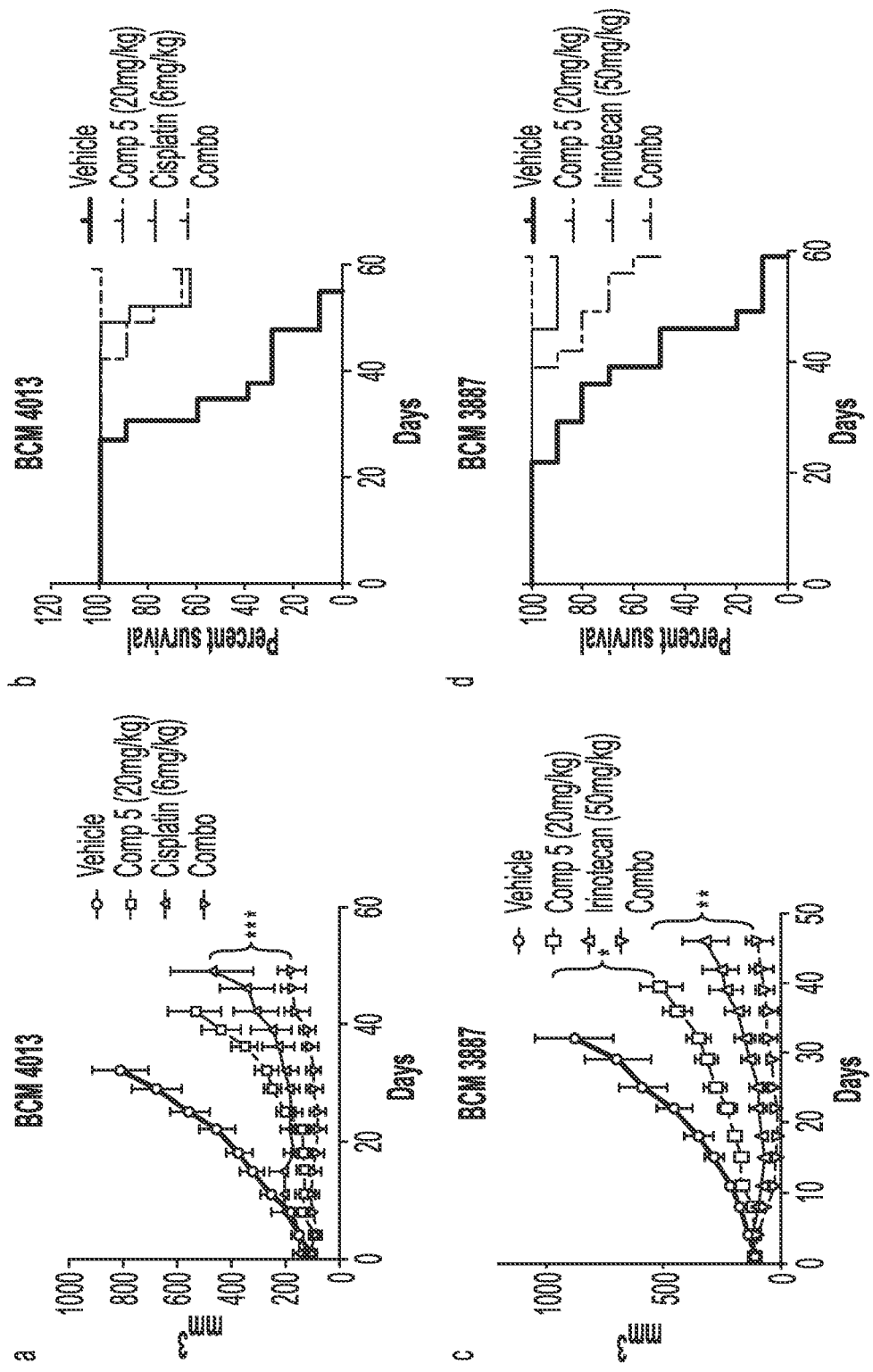
FIGS. 9a, 9b, 9c, and 9d. Anti-TNBC pre-clinical efficacy studies. a) Growth curves (left), survival (right) of orthotopic implantation of BCM-4013 tumors in mice treated with vehicle (black line), compound 5, (red line), cisplatin (blue line or compound 5 and cisplatin (green line. b) Growth curves (left), survival (right) of orthotopic implantation of BCM-3887 tumors in mice treated with vehicle (black line), compound 5, (red line), irinotecan (blue line or compound 5 and irinotecan (green line. *P=0.05, *** p=0.001).

The anti-breast cancer efficacy of compound 5 was tested in vivo using primary patient-derived xenograft (PDX) models, both as a monotherapy and in combination with clinical agents in these pre-clinical models. BCM-4013 is a BRCA proficient PDX model derived from a patient with basal-like invasive ductal carcinoma that metastasized to the patients' lungs and that only partially responded to combination Dasatinib/Docetaxel treatment. Importantly, there is high concordance between patient and mouse efficacy studies for each of the PDX models presented.[2] BCM-4013 explants were implanted into the cleared mammary fat-pad of SCID/Beige recipient mice. After tumors reached 100-mm$^3$, mice were randomized and treated with vehicle, compound 5, Cisplatin or the combination of compound 5 and Cisplatin as outlined in the methods (FIG. 9a). Notably, while compound 5 was as effective as Cisplatin as a mono agent the combination was significantly more effective ($p<0.001$) than either single agent alone. We next tested compound 5 in the BRCA-deficient PDX, BCM-3887. In this study compound 5 significantly delayed tumor growth ($p<0.05$) and was highly effect in combination with irinotecan, where 4 out of the 8 mice lacked detectable tumors (FIG. 9b).

Figure 10:
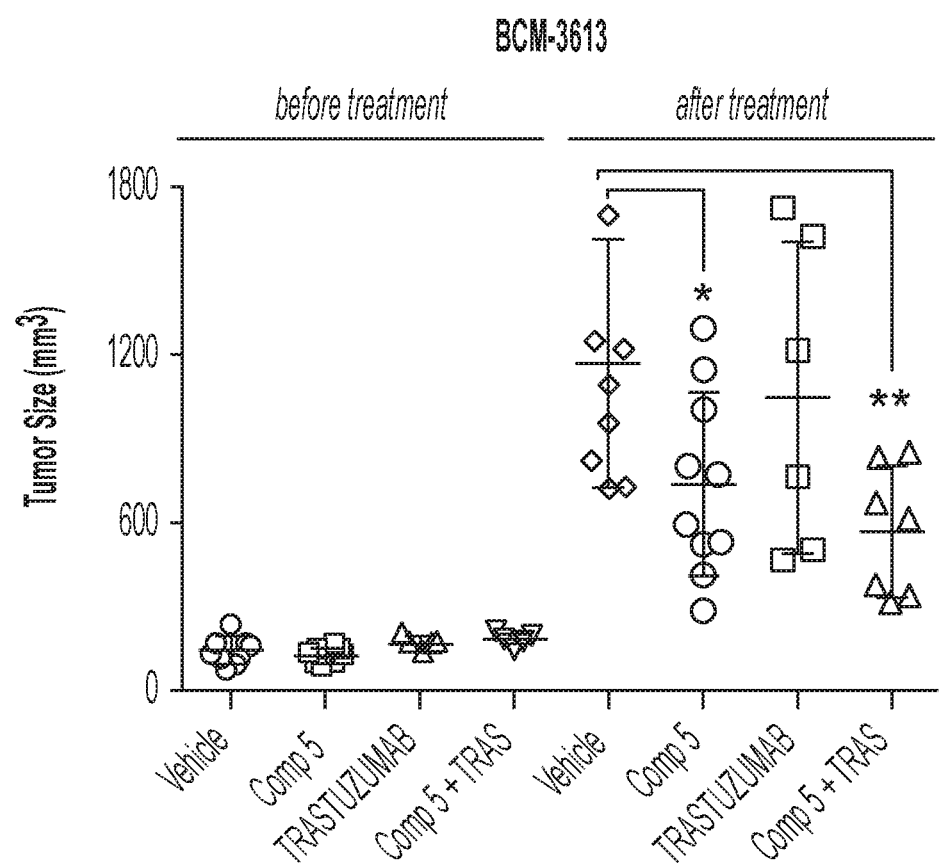
FIG. 10. Growth of orthotopic implantation of BCM-3613 tumors in mice before and after treatment with indicated agents. *P=0.05, *19=0.01.

Our in vitro cell-based combination studies indicate that compound 5 acts in synergy with anti-HER2+ target therapies in both anti-HER2+ sensitive and resistant cell lines. BCM-3613 is a PDX model derived from a patient that acquired resistance to trastuzumab. BCM-3613 explants were implanted into the cleared mammary fat-pad of SCID/Beige recipient mice. After tumors reached 100-mm$^3$, mice were randomized and treated with vehicle, compound 5, trastuzumab or the combination of compound 5 and trastuzumab as outlined in the methods (FIG. 10) While, trastuzumab demonstrated no efficacy over vehicle treated cohort, compound 5 significantly delayed tumor growth as a single agent ($p=0.05$) and sensitized these tumor to trastuzumab ($p=0.01$).

EXAMPLES

Biological Studies

Studies were performed to determine the efficacy of the highly specific dual CDK12/CDK13 or single CDK13 inhibitors in pre-clinical models of human breast cancer. Four patient derived orthotopic breast xenograft models were used to validate targeting CDK12/13 or CDK13 alone as an anti-cancer strategy in subsets of breast cancer. Power analyses suggested that based on the difference in tumor volume between groups and the standard deviation of tumor volumes within each group for confidence of 90%, an n of at least 7 or greater is required. Experiments therefore included 7-12 tumor bearing mice per experimental or control (vehicle) cohort with mice randomized prior to treatment to determine random sampling such that the median tumor size between cohorts was the same. All tumors sizes were measured throughout the duration of the experiment and graphed in figures without excluding any samples. For survival analyses, mice were euthanized when moribund, and/or when tumors became ulcerated or reached greater than 1.0 cm$^3$. All cell-based assays were performed in triplicate and repeated at least 3 times. Some pharmacokinetic data are shown in Table 3, above.

Reagents

Unless otherwise stated all chemicals were purchased from Sigma Aldrich. MDA-MB-231, MDA-MB-436, MDA-MB-468, BT474, SKBR3, MDA-MB-453, MCF7 and T47D breast cancer cells were purchased from the American Type Culture Collection (ATCC). BT474 and SKBR3 lapatinib resistant cell lines were a gift from Dr. Gary Johnson (University of North Carolina, NC).

Cell Proliferation and Clonogenicity Assays.

Cell proliferation was measured 72 hr after compound or vehicle treatment using Cell-Titer Glo (Promega) according to the manufacturers' instructions. $EC_{50}$ values were determined using non-linear regression and a four-parameter algorithm (GraphPad Prism5). For clonogenic assays, cells were plated in 6-well dishes in triplicate at a density of 500-1000 cells per well. After overnight incubation, compound or vehicle (DMSO) was added to media for 72 hr and cells were allowed to grow out for 7-10 days, during which media was changed every 2-3 days in the absence of compound. Colonies were fixed in 4% paraformaldehyde/PBS and stained with 0.5% Crystal Violet in 25% methanol for 30 min at room temperature and de-stained with water. Colonies with greater than 50 cells were counted using a low magnification light microscope.

Detection of pSer2 of Rpb1 (Subunit of PolI®) by In-Cell Western Using the LI-COR Odyssey Infrared Imaging System.

MDA-MB-231 cells were plated at 5000 cells/well in a 384-well optical bottom plates (Nunc) in DMEM-10% FBS. Following attachment cells were treated with test compound in 0.4% DMSO (final concentration) for 4 hours at 37 C. Cells were fixed with 4% paraformaldehyde for 30 min, washed in PBS, and permeabilized in 0.3% Triton X100 for 15 min. Cells were washed in PBS and blocked in Li-COR blocking buffer for 2 hr at room temperature. Cells were probed for pSer2 Rpb1 using E1Z3Gabbit primary antibody (#13499, Cell Signaling) and for total Rpb1 CTD using 4H8 mouse primary antibody (#2629, Cell Signaling) incubated overnight at 4 C. Following washing with PBS-0.1% Tween 20, cells were probed with goat-anti rabbit IR800 antibody (926-32211, Li-Cor) and goat-anti mouse IR680 (926-68070, Li-Cor) for 1 hr at room temperature. After intensive washing with PBS-0.1% Tween 20, plates were imaged using the Odyssey infrared imaging system (Li-COR Biosciences).

Xenograft Tumor Models.

All animal studies are approved by the Scripps Florida IACUC. Establishment of BCM-4013, BCM-3887, BCM3613 and BCM3963 patient derived xenografts were as described.[1] Briefly, fresh xenograft tumor fragments (~1 mm$^3$) were transplanted into the cleared mammary fat pad of recipient SCID/Bg mice (Charles River Laboratories). Tumor growth was measured in two dimensions using calipers and tumor volume calculated ($v=0.5\times\text{length}\times\text{width}^2$). Animals with established tumors (mean tumor volume ~100 mm$^3$) were randomly divided into treatment cohorts. Mice were treated with compound 5 (20 mg/kg daily by p.o) cisplatin (6 mg/kg by i.p.), irinotecan (50 mg/kg by i.p.), or vehicle (10% DMSO/90% of a 30% solution of hydroxypropyl-β-cyclodextran in water). Growth rates were monitored at indicated times and tumors were harvested for histopathology and lysate preparation for western blotting once vehicle treated tumors reached 0.8-1 cm$^3$.

Immunoblotting.

SDS-PAGE gel electrophoresis was performed using NuPAGE 4-12% Bis-Tris gels (Invitrogen) and transferred to 0.4% nitrocellulose membranes by semi-dry transfer using trans-blot transfer medium (Biorad). Membranes were blocked in Odyssey blocking buffer (LI-COR Biosciences) and incubated overnight at 4° C. with primary antibodies. After repeated washes with TBST (20 mM Tris, pH 7.6, 140 mM NaCl and 0.1% Tween-20) blots were incubated with the appropriate IRDye-conjugated secondary antibody (LI-COR Biosciences) and imaged using the LI-COR Odyssey. Bands were quantified using the Odyssey software (LI-COR Biosciences).

Endogenous CDK12 and CDK13 Gene Knockout Using Crispr/Cas9

Crispr lentiviral constructs containing guide RNA sequences directed against CDK12 and CDK13 were purchased from GenScript in LentiCRISPR v2 backbone, Cdk12 gRNA sequence (SEQ ID NO: 1)
TGGCTCAGCTAGAACTGATC.

Cdk13 gRNA sequence (SEQ ID NO: 2)
ATATATGGACCATGATCTGA.

LentiCRISPR v2 empty, Cdk12 or Cdk13 were co-transfected individually with MISSION Lentiviral packaging mix (SHP001, Sigma) into HEK293T cells using Lipofectamine 3000 (L3000015, ThermoFisher Scientific) in order to produce lentiviral particles as per the manufacturers' recommendations. MDA-MB-231 cells were transduced with optimized titers of lentiviruses and infected cells were selected in puromycin (1 μg/ml)

RT-PCR

Total cellular RNA was isolated from cells using RNase mini kit (Qiagen) and 1.0 μg was reverse transcribed into cDNA SuperScript III First-Strand Synthesis System (18080051, Life Technologies). Quantitative PCR reactions were performed in an ABI Prism 7300 platform (Life Technologies). CDK12 expression was assessed using the following primer sets: forward (SEQ ID NO: 3)
5'-CCAATCTGGAACTGGCTCAG-3';

reverse (SEQ ID NO: 4)
5'-CAAGTGCTGCAGAAGGAATG-3'.

CDK13 expression was assessed using the following primer sets: forward (SEQ ID NO: 5)
5'-GGTGTTTGAATATATGGACC-3';

reverse (SEQ ID NO: 6)
5'-CAAGTCCAAAGTCTGCAAGTT-3'

CDK12 and CDK13 primer sets were designed using Primer 3 software. Relative gene expression was normalized to human GAPDH using the following primer sets: forward (SEQ ID NO: 7)
5'-TCACCAGGGCTGCTTTTAAC-3';

reverse (SEQ ID NO: 8)
5'-ATCTCGCTCCTGGAAGATGG-3'.

Compounds of the invention were prepared according to the synthetic schemes and procedures disclosed below.

Scheme 1. General strategy for the synthesis of N9-1-methyl-1H-pyrazol-4-yl CDK12/13 inhibitors

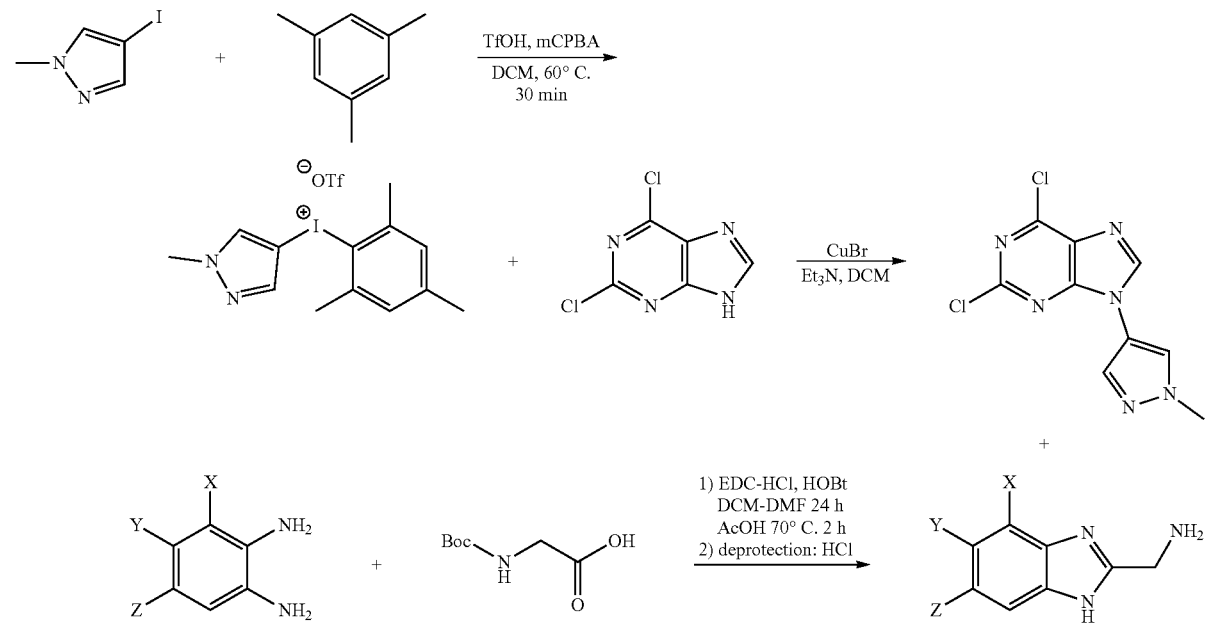

-continued
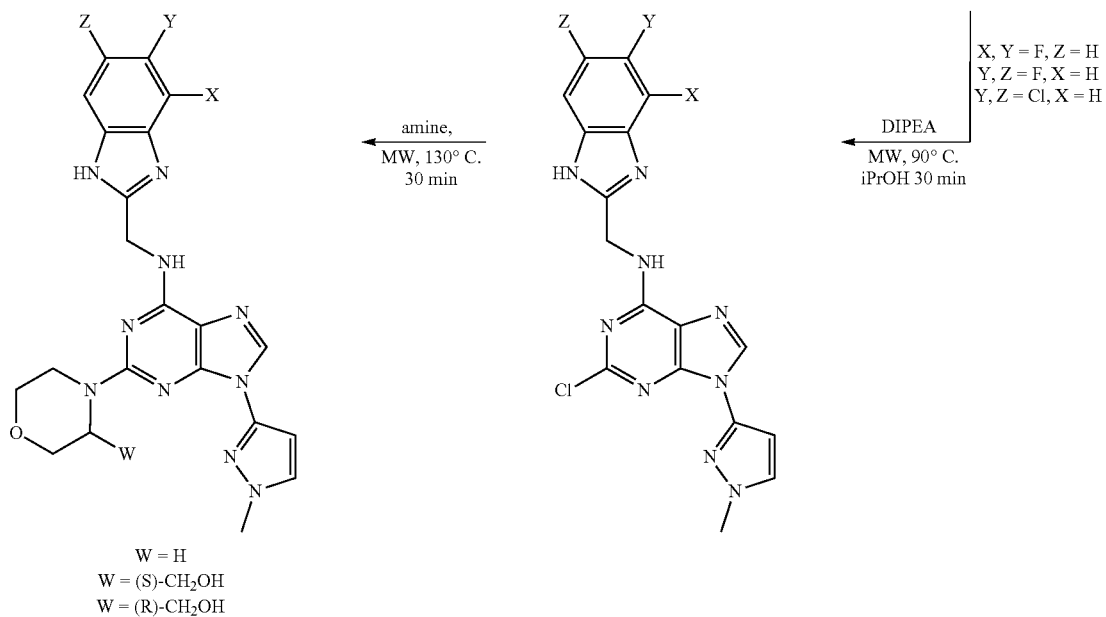
W = H
W = (S)-CH$_2$OH
W = (R)-CH$_2$OH
X, Y = F, Z = H
Y, Z = F, X = H
Y, Z = Cl, X = H
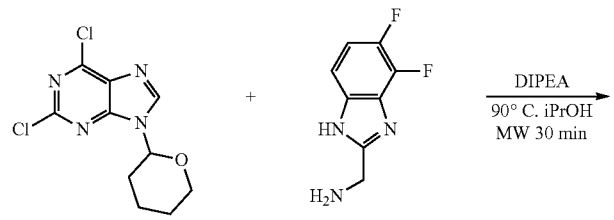
Scheme 2. General strategy for the synthesis of N9-thiazoles CDK12/13 inhibitors
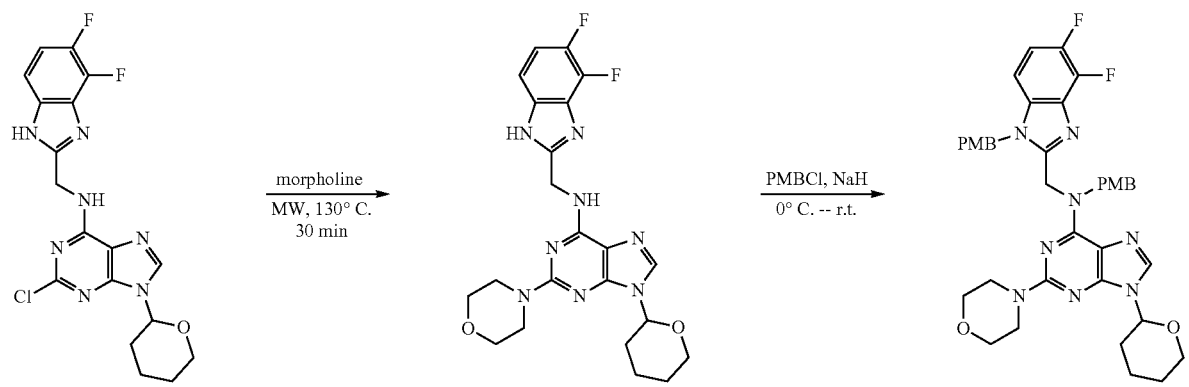

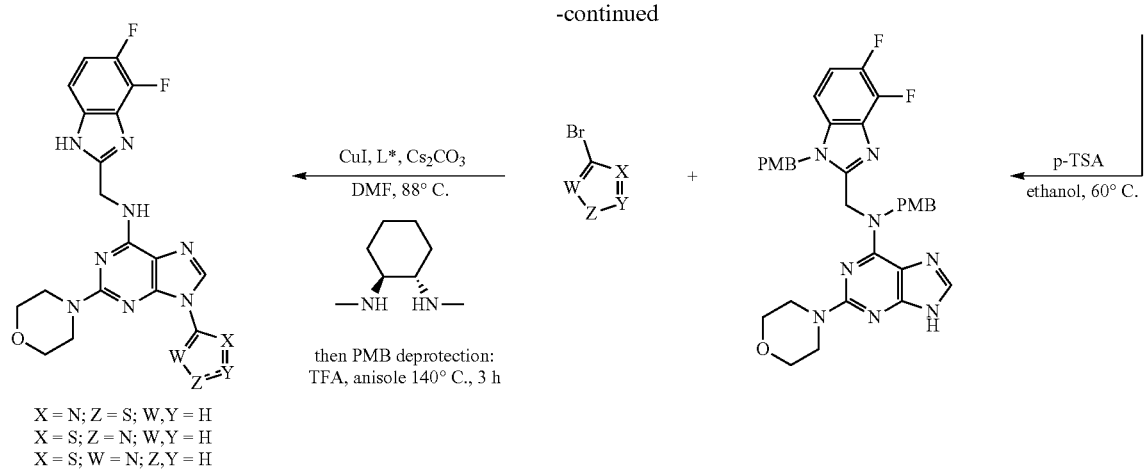

X = N; Z = S; W,Y = H
X = S; Z = N; W,Y = H
X = S; W = N; Z,Y = H

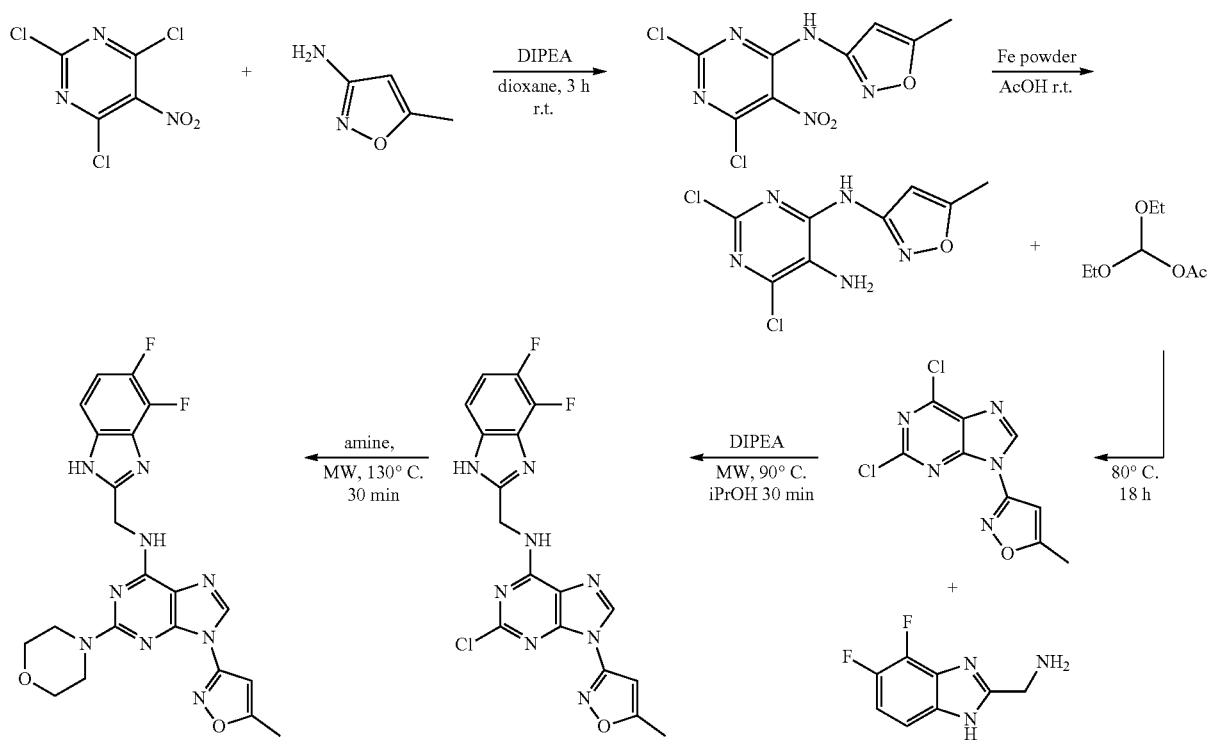

Scheme 3. Synthesis of compound 3

Chemical Studies

All reagents were purchased from commercial suppliers and were used without further purification. Dichloromethane, diethyl ether, N,N-dimethylformamide and tetrahydrofuran were dried by being passed through a column of desiccant (activated A-1 alumina). Triethylamine and diisopropyl amine was purified by distillation from calcium hydride. Reactions were either monitored by thin layer chromatography or analytical LC-MS.

Thin layer chromatography was performed on Kieselgel 60 F254 glass plates pre-coated with a 0.25 mm thickness of silica gel. TLC plates were visualized with UV light and/or by staining with ninhydrin solution. Normal phase column chromatography was performed on a Biotage Isolera automated flash system. Compounds were loaded onto pre-filled cartridges filled with KP-Sil 50 μm irregular silica. For microwave reactions, a Biotage Initiator Microwave system was used. Some of the final products were isolated by reverse-phase HPLC using Shimadzu Prep LC system with photodiode array detector, Waters SunFire C18 OBD Prep Column, 100 Å, 10 μm, 30 mm×250 mm. Compounds were eluted using a gradient elution of 90/10 to 0/100 A/B over 10 min at a flow rate of 50.0 mL/min, where solvent A was water (+0.1% TFA) and solvent B was acetonitrile/methanol (1:1).

The structures of all compounds were verified via $^1$H NMR, $^{13}$C NMR, $^{19}$F NMR and HPLC/LCMS. The purity of isolated products was determined using an LC-MS instrument (Agilent 1260 Infinity series LC with 500 Ion Trap MS) equipped with Kinetex® 5 μm EVO C18 100 Å LC Column 100×4.6 mm (Phenomenex) column. Elution was performed using the following conditions: 2% (v/v) acetonitrile (+0.1% FA) in 98% (v/v) H$_2$O (+0.1% FA), ramped to 98% acetonitrile over 8 min, and holding at 98% acetonitrile for 1 min with a flow rate of 1.75 mL/min; UV absorption was detected from 200 to 950 nm using a diode array detector. The purity of each compound was ≥95% based on this analysis.

NMR spectra were recorded at ambient temperature on a 400 or 700 MHz Bruker NMR spectrometer in DMSO-d6. All $^1$H NMR data are reported in parts per million (ppm) downfield of TMS and were measured relative to the signals for dimethyl sulfoxide (2.50 ppm). All $^{13}$C NMR spectra are reported in ppm relative to the signals for dimethyl sulfoxide (39.5 ppm) with $^1$H decoupled observation. $^{19}$F NMR experiments were performed with $^1$H decoupling. Data for $^1$H NMR are reported as follows: chemical shift (δ, ppm), multiplicity (s=singlet, d=doublet, t=triplet, q=quartet, m=multiplet), integration, and coupling constant (Hz), whereas $^{13}$C NMR analyses were obtained at 101 and reported in terms of chemical shift. NMR data was analyzed and processed by using MestReNova software. High-resolution mass spectra were recorded on a spectrometer (ESI-TOF) at the University of Illinois Urbana-Champaign Mass Spectrometry Laboratory.

The synthesis and analysis of 2,6-dichloro-9-aryl-9H-purines 5 benzimidazoles 8 were previously described.[2-4] Diaryliodonium salts 5 were prepared according to the reported procedures.[5-6] Newly synthesized compounds described below.

4-(mesityl-λ$^2$-iodanyl)-1-methyl-1H-pyrazole trifluoromethanesulfonate

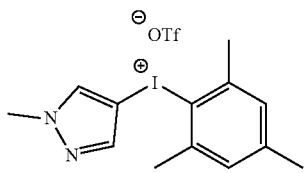

The compound was prepared according to the reported procedures in 90% yield.[5-6] To a solution of 4-iodo-1-methyl-1H-pyrazole (10.0 g, 48.1 mmol) in DCM (192 ml) was added triflic acid (17.08 ml, 192 mmol) and the resulting mixture was stirred at room temperature for 5 min. mCPBA (12.44 g, 72.1 mmol) followed by mesitylene (6.36 g, 52.9 mmol) was then added (in this order). The reaction vessel was sealed and submitted to a 60° C. oil bath with stirring for 30 min. The reaction mixture was then allowed to reach rt after which it was concentrated in vacuo followed by precipitation by addition of Et$_2$O (100 mL). The mixture was stirred at 0° C. for additional 30 min. The solid was collected by filtration and washed with Et$_2$O. LCMS m/z 327.3. $^1$H NMR (400 MHz, DMSO-d$_6$) δ 9.78 (s, 1H), 8.55 (s, 1H), 8.06 (s, 1H), 7.16 (s, 2H), 3.89 (s, 3H), 2.64 (s, 6H), 2.26 (s, 3H). $^{13}$C NMR (101 MHz, DMSO-d$_6$) δ 143.02, 142.90, 140.86, 137.02, 129.59, 124.58, 120.80 (q, J=322.3 Hz), 79.06, 39.43, 26.43, 20.56. $^{19}$F NMR (376 MHz, DMSO-d$_6$) δ −77.76.

2,6-dichloro-9-(1-methyl-1H-pyrazol-4-yl)-9H-purine

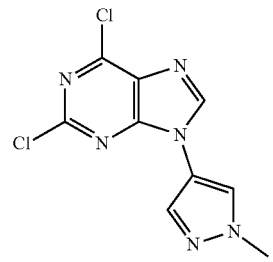 [SMILES: Cn1cc(-n2cnc3c(Cl)nc(Cl)nc32)cn1]

The compound was prepared according to the reported procedures in 57% yield.[3] 2,6-dichloro-9H-purine (9.16 g, 48.5 mmol), copper(I) bromide (1.390 g, 9.69 mmol) and 4-(mesityl-λ$^2$-iodanyl)-1-methyl-1H-pyrazole trifluoromethanesulfonate (30 g, 63.0 mmol) in dichloromethane (194 ml) were mixed in 500 ml round bottom flask (previously backfilled with argon). Then TEA (10.13 ml, 72.7 mmol) was added dropwise. The resulting mixture was heated 60° C. for 4 h and monitored by LCMS. Upon consumption of all salt, the reaction mixture was concentrated in vacuo and the crude product was purified by flash chromatography (hexane:EtOAc). LCMS m/z 269.3 (M+1). $^1$H NMR (400 MHz, DMSO-d$_6$) δ 9.00 (s, 1H), 8.36 (d, J=0.8 Hz, 1H), 7.97 (d, J=0.8 Hz, 1H), 3.96 (s, 3H). $^{13}$C NMR (101 MHz, DMSO-d$_6$) δ 152.54, 151.60, 150.02, 147.17, 132.54, 130.58, 125.27, 116.15, 39.31.

tert-butyl ((5,6-dichloro-1H-benzo[d]imidazol-2-yl)methyl)carbamate

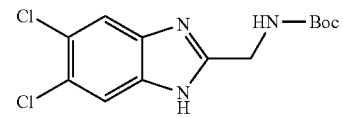 [SMILES: CC(C)(C)OC(=O)NCc1nc2cc(Cl)c(Cl)cc2[nH]1]

The compound was prepared according to the reported procedures.[2] A 250 ml round bottom flask was charged with (tert-butoxycarbonyl)glycine (4.95 g, 28.2 mmol), EDC (6.50 g, 33.9 mmol)), HOBT (6.06 g, 39.5 mmol) and DCM (282 ml). The mixture was stirred at room temperature for 10 min. 4,5-dichlorobenzene-1,2-diamine (5.0 g, 28.2 mmol) and DMF (2 ml) were then added. The mixture was stirred overnight at room temperature. DCM was evaporated and ethyl acetate was added (50 ml). The organic phase was washed 2 times with brine (20 ml), 2 times with NH$_4$Cl (saturated in water), 2 times with NaHCO$_3$ (saturated in water) and finally once with brine. The organic layer was dried over Na$_2$SO$_4$ and the solvent was evaporated under reduced pressure. 32 ml of acetic acid were added and this mixture was heated for 2 h at 70° C. After evaporation the obtained mixture was precipitated in methylene chloride:Et$_2$O:MeOH (90:8:2) and filtered to afford 6.3 g as a white solid (71% yield). LCMS m/z 317.0 (M+1). $^1$H NMR (400

MHz, DMSO-d$_6$) δ 12.51 (s, 1H), 7.75 (s, 2H), 7.48 (t, J=5.9 Hz, 1H), 4.35 (d, J=5.9 Hz, 2H), 1.40 (s, 9H). b (5,6-dichloro-1H-benzo[d]imidazol-2-yl)methanamine hydrochloride

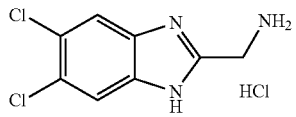 [SMILES: NCc1nc2cc(Cl)c(Cl)cc2[nH]1 ; Cl]

tert-butyl ((5,6-dichloro-1H-benzo[d]imidazol-2-yl)methyl)carbamate (8 g, 25.3 mmol) was added to 250 ml round bottom flask at r.t following by addition of ethyl acetate (101 ml) and 12M HCl (21.08 ml, 253 mmol). Reaction mixture was allowed to stir overnight. White precipitate (96% yield) was filtered and washed with Et$_2$O. LCMS m/z 216.4 (M+1). $^1$H NMR (400 MHz, DMSO-d$_6$) δ 9.89 (s, 1H), 8.90 (s, 3H), 7.93 (s, 2H), 4.34 (d, J=5.2 Hz, 2H).

N-((5,6-dichloro-1H-benzo[d]imidazol-2-yl)methyl)-9-(1-methyl-1H-pyrazol-4-yl)-2-morpholino-9H-purin-6-amine (Compound 5)

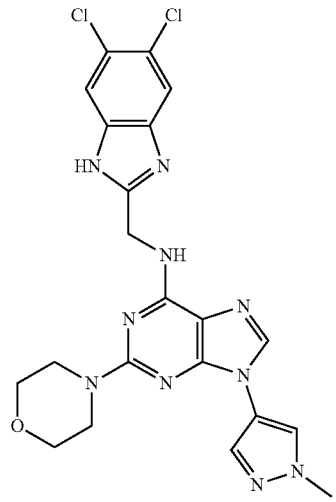 [SMILES: Cn1cc(-n2cnc3c(NCc4nc5cc(Cl)c(Cl)cc5[nH]4)nc(N4CCOCC4)nc32)cn1]

Compound 5 was prepared according to the reported procedures.[7] 2,6-dichloro-9-(1-methyl-1H-pyrazol-4-yl)-9H-purine (6 g, 22.30 mmol), (5,6-dichloro-1H-benzo[d]imidazol-2-yl)methanamine, 2HCl (6.77 g, 23.41 mmol) were charged into 250 round bottom flask followed by addition of 2-propanol (89 ml) at r.t. Then DIPEA (19.47 ml, 111 mmol) was added to the suspension and vial was heated in conventional oil bath at 90° C. for 60 mins. The reaction mixture was allowed to reach room temperature, then precipitate was filtered and washed with Et$_2$O (LCMS m/z 449.7 (M+1). 2-chloro-N-((5,6-dichloro-1H-benzo[d]imidazol-2-yl)methyl)-9-(1-methyl-1H-pyrazol-4-yl)-9H-purin-6-amine (8 g, 17.83 mmol) was added to 250 ml round bottom flask followed by addition of morpholine (15.53 ml, 178 mmol). Mixture was stirred at 130° C. for 30 min. The reaction mixture was concentrated under reduced pressure and the crude product was purified by flash chromatography (DCM:MeOH, 10:1, gradient). Fractions containing product were combined, and organic phase was washed 2 times with NH$_4$Cl (to remove residual morpholine), and finally once with brine. The organic layer was dried over Na$_2$SO$_4$ and the solvent was evaporated under reduced pressure to yield compound 5 as white solid (74% yield over two steps). LCMS m/z 500.7 (M+1). $^1$H NMR (400 MHz, DMSO-d$_6$) δ 8.31 (s, 1H), 8.21 (s, 2H), 7.99 (s, 1H), 7.71 (s, 2H), 4.82 (s, 2H), 3.91 (s, 3H), 3.58-3.45 (m, 8H). $^{13}$C NMR (101 MHz, DMSO-d$_6$) δ 158.68, 156.53, 154.03, 150.17, 137.49, 136.35, 130.75, 124.18, 122.88, 118.63, 115.89, 113.46, 65.99, 44.56, 39.16, 38.54.

N-((4,5-difluoro-1H-benzo[d]imidazol-2-yl)methyl)-9-(1-methyl-1H-pyrazol-4-yl) morpholino-9H-purin-6-amine (Compound 1)

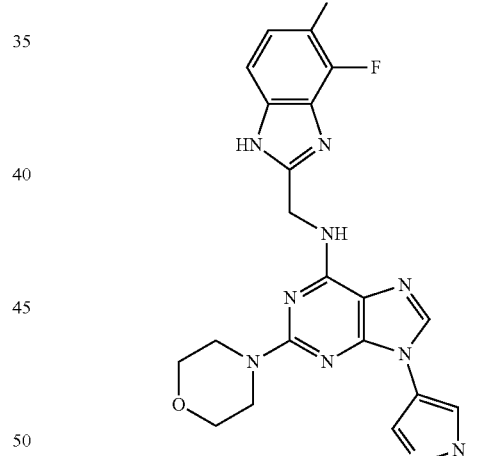

Compound 1 was prepared according to Scheme 1 using the procedure for compound 5 in 54% yield over two steps as a white solid.[7] LCMS m/z 467.6 (M+1). $^1$H NMR (400 MHz, DMSO-d$_6$) δ 12.52 (s, 1H), 8.31 (s, 1H), 8.20 (s, 2H), 7.99 (s, 1H), 7.26-7.12 (m, 2H), 4.82 (s, 2H), 3.60-3.43 (m, 8H). $^{19}$F NMR (376 MHz, DMSO-d$_6$) δ −148.66 (d, J=22.3 Hz), −150.47 (d, J=21.4 Hz), 155.44 (d, J=21.7 Hz), −155.82 (d, J=21.4 Hz).

(S)-(4-(6-(((5,6-dichloro-1H-benzo[d]imidazol-2-yl)methyl)amino)-9-(1-methyl-1H-pyrazol-4-yl)-9H-purin-2-yl)morpholin-3-yl)methanol (Compound 6)

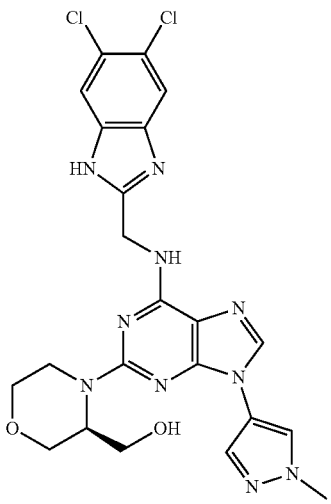 [SMILES: Cn1cc(-n2cnc3c(NCc4nc5cc(Cl)c(Cl)cc5[nH]4)nc(N4CCOC[C@@H]4CO)nc32)cn1]

Compound 6 was prepared according to Scheme 1 using the procedure for compound 5 in 24% yield over two steps as a white solid.[7] LCMS m/z 529.9 (M+1). $^1$H NMR (400 MHz, DMSO-d$_6$) δ 12.37 (s, 1H), 8.29 (s, 1H), 8.18 (s, 1H), 8.15 (s, 1H), 8.00 (s, 1H), 7.79 (s, 1H), 7.66 (s, 1H), 4.90-4.78 (m, 3H), 4.44 (s, 1H), 4.24 (d, J=13.6 Hz, 1H), 3.97 (d, J=11.5 Hz, 1H), 3.91 (s, 3H), 3.79 (d, J=11.1 Hz, 1H), 3.64 (d, J=8.2 Hz, 1H), 3.47-3.35 (m, 3H), 2.97 (t, J=12.9 Hz, 1H).

(R)-(4-(6-(((5,6-dichloro-1H-benzo[d]imidazol-2-yl)methyl)amino)-9-(1-methyl-1H-pyrazol-4-yl)-9H-purin-2-yl)morpholin-3-yl)methanol (Compound 7)

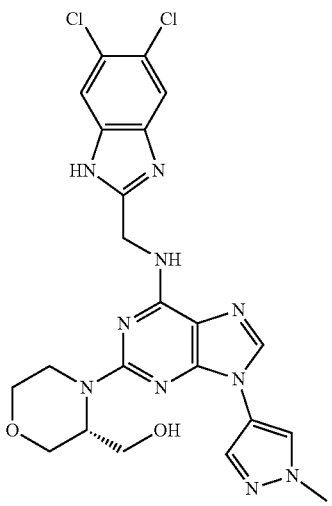 [SMILES: Cn1cc(-n2cnc3c(NCc4nc5cc(Cl)c(Cl)cc5[nH]4)nc(N4CCOC[C@H]4CO)nc32)cn1]

Compound 7 was prepared according to Scheme 1 using the procedure for compound 5 in 21% yield over two steps as a white solid.[7] LCMS m/z 529.9 (M+1). $^1$H NMR (400 MHz, DMSO-d$_6$) δ 12.37 (s, 1H), 8.29 (s, 1H), 8.18 (s, 1H), 8.15 (s, 1H), 8.00 (d, J=0.7 Hz, 1H), 7.79 (s, 1H), 7.66 (s, 1H), 4.98-4.73 (m, 3H), 4.44 (s, 1H), 4.24 (d, J=13.6 Hz, 1H), 3.97 (d, J=11.7 Hz, 1H), 3.91 (s, 3H), 3.79 (d, J=11.0 Hz, 1H), 3.64 (d, J=7.7 Hz, 1H), 3.46-3.34 (m, 3H), 3.05-2.92 (m, 1H).

N-((5,6-difluoro-1H-benzo[d]imidazol-2-yl)methyl)-9-(1-methyl-1H-pyrazol-4-yl) morpholino-9H-purin-6-amine (Compound 2)

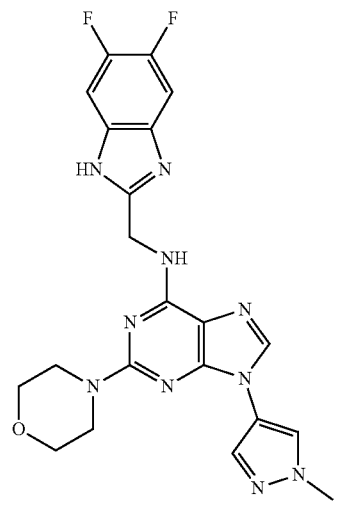 [SMILES: Cn1cc(-n2cnc3c(NCc4nc5cc(F)c(F)cc5[nH]4)nc(N4CCOCC4)nc32)cn1]

Compound 2 was prepared according to Scheme 1 using the procedure for compound 5 in 63% yield over two steps as a white solid.[7] LCMS m/z 467.5 (M+1). $^1$H NMR (400 MHz, DMSO-d$_6$) δ 12.32 (s, 1H), 8.31 (d, J=0.7 Hz, 1H), 8.20 (s, 1H), 8.15 (s, 1H), 7.99 (d, J=0.7 Hz, 1H), 7.56 (dd, J=7.5, 11.3 Hz, 1H), 7.41 (dd, J=7.4, 10.5 Hz, 1H), 4.80 (s, 2H), 3.91 (s, 3H), 3.60-3.45 (m, 8H). $^{19}$F NMR (376 MHz, DMSO-d$_6$) δ −144.97 (d, J=22.2 Hz), −146.40 (d, J=22.2 Hz).

N-((4,5-difluoro-1H-benzo[d]imidazol-2-yl)methyl)-2-morpholino-9-(tetrahydro-2H-pyran-2-yl)-9H-purin-6-amine

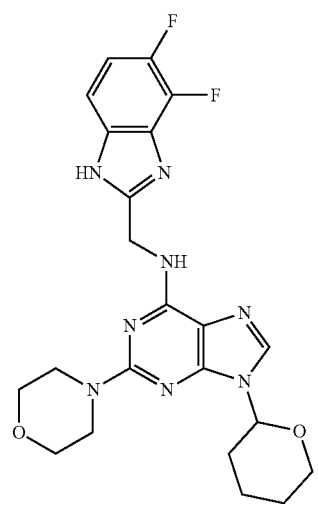 [SMILES: Fc1ccc2[nH]c(CNc3nc(N4CCOCC4)nc4c3ncn4C3CCCCO3)nc2c1F]

2,6-dichloro-9-(tetrahydro-2H-pyran-2-yl)-9H-purine (0.25 g, 0.915 mmol), (4,5-difluoro-1H-benzo[d]imidazol-2-yl)methanamine, 2HCl (0.246 g, 0.961 mmol) were charged into small MW vessel followed by addition of 2-propanol (3.66 ml) at r.t. under normal conditions. Then DIPEA (0.799 ml, 4.58 mmol) was added to the suspension and vial was sealed and heated in MW at 90° C. for 30 mins. The reaction mixture was allowed to reach room temperature, and then precipitate was filtered and washed with Et$_2$O (yield 81%). LCMS m/z 420.3 (M+1). 2-chloro-N-((4,5-difluoro-1H-benzo[d]imidazol-2-yl)methyl)-9-(tetrahydro-2H-pyran-2-yl)-9H-purin-6-amine (0.31 g, 0.738 mmol) was added to small 5 ml MW vial followed by addition of morpholine (1.846 ml, 0.738 mmol). Mixture was stirred at 130° C. MW for 30 min. The reaction mixture was concentrated under reduced pressure and the crude product was purified by flash chromatography (DCM:MeOH, 10:1, gradient) to obtain 0.3 g of product as white solid (88% yield). LCMS m/z 471.4 (M+1).

N-((4,5-difluoro-1-(4-methoxybenzyl)-1H-benzo[d]imidazol-2-yl)methyl)-N-(4-methoxybenzyl)-2-morpholino-9-(tetrahydro-2H-pyran-2-yl)-9H-purin-6-amine

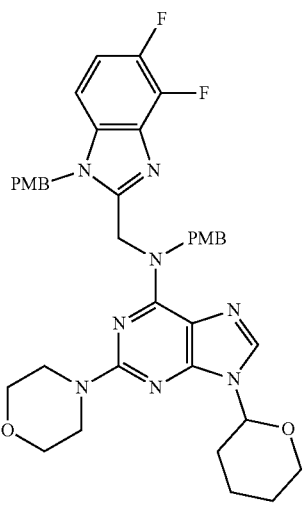

To a 5 ml MW vial (previously backfilled with argon) was added NaH (60% in mineral oil, sodium hydride (0.013 g, 0.319 mmol)) and THF (1.063 ml). The mixture was cooled to about 0° C. N-((4,5-difluoro-1H-benzo[d]imidazol-2-yl)methyl)-2-morpholino-9-(tetrahydro-2H-pyran-2-yl)-9H-purin-6-amine (0.05 g, 0.106 mmol) was added in several smaller portions and the mixture was stirred at about 0° C. for 20 min. 4-methoxybenzyl chloride (0.043 ml, 0.319 mmol) was added dropwise and the mixture was stirred at about 0° C. for about 10 min and then heated at 60° C. for 24 h. To the mixture was added statured aqueous NH$_4$Cl (25 mL) and water (10 mL). The aqueous layer was separated and extracted with EtOAc (2*50 mL). The combined organic layers were washed with brine (50 mL) dried over sodium sulfate, filtered and concentrated under reduced pressure. The residue was purified by column chromatography to obtain 0.073 g of product (97% yield). LCMS m/z 711.8 (M+1).

N-((4,5-difluoro-1-(4-methoxybenzyl)-1H-benzo[d]imidazol-2-yl)methyl)-N-(4-methoxybenzyl)-2-morpholino-9H-purin-6-amine

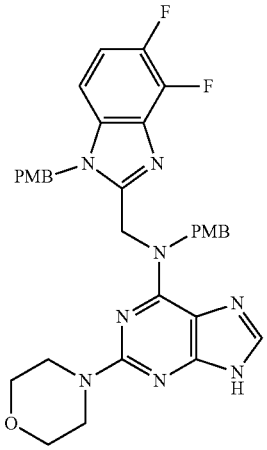

N-((4,5-difluoro-1-(4-methoxybenzyl)-1H-benzo[d]imidazol-2-yl)methyl)-N-(4-methoxybenzyl)-2-morpholino-9-(tetrahydro-2H-pyran-2-yl)-9H-purin-6-amine (0.073 g, 0.103 mmol) was dissolved in ethanol (2.054 ml) followed by addition of p-toluenesulfonic acid monohydrate (0.021 g, 0.113 mmol). The reaction was heated to 60° for 4 h. Solvent was removed and residue re-dissolved in EtOAc and washed with NaHCO$_3$, water, and brine. The organic layer was dried over Na$_2$SO$_4$ and the solvent was evaporated under reduced pressure followed by precipitation by addition of petroleum ether:Et$_2$O (5:1). LCMS m/z 627.7 (M+1).

N-((4,5-difluoro-1H-benzo[d]imidazol-2-yl)methyl)-2-morpholino-9-(thiazol-4-yl)-9H-purin-6-amine (Compound 4)

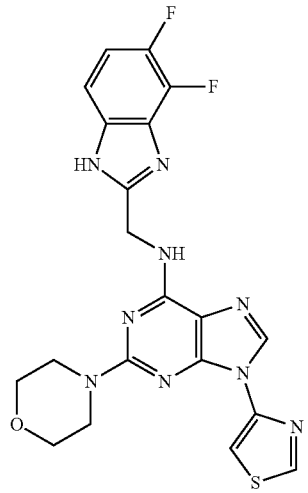 [SMILES: Fc1ccc2[nH]c(CNc3nc(N4CCOCC4)nc4c3ncn4-c3cscn3)nc2c1F]

Compound 4 was prepared as described in Scheme 2. The deprotected N-((4,5-difluoro-1-(4-methoxybenzyl)-1H-benzo[d]imidazol-2-yl)methyl)-N-(4-methoxybenzyl)-2-morpholino-9H-purin-6-amine (0.06 g, 0.096 mmol), copper (I) iodide (9.12 mg, 0.048 mmol) and cesium carbonate (0.094 g, 0.287 mmol) are combined in small MW vial (previously backfilled with argon). (1S,2S)—N1,N2-dimethylcyclohexane-1,2-diamine (6.81 mg, 0.048 mmol) and 4-bromothiazole (0.018 ml, 0.191 mmol) in DMF (0.191 ml) are then added and the mixture stirred at 88° C. overnight. The mixture was diluted with water and extracted ×3 EtOAc. The combined organic layers were washed with brine (50 mL) dried over sodium sulfate, filtered and concentrated under reduced pressure. The residue was purified by column chromatography (hexane:EtOAc) to obtain 0.04 g of product (59% yield). N-((4,5-difluoro-1-(4-methoxybenzyl)-1H-benzo[d]imidazol-2-yl)methyl)-N-(4-methoxybenzyl)-2-morpholino-9-(thiazol-4-yl)-9H-purin-6-amine (0.040 g, 0.056 mmol) was dissolved in TFA (0.939 ml) followed by addition of 1,4-dioxane (0.939 ml) and anisole (0.062 ml, 0.564 mmol) in 5 ml MW and heated for 3 h at 140° C. The solvent was removed under reduced pressure, the residue re-dissolved in DCM:MeOH (10:1) mixture and then washed with NaHCO$_3$, water, and brine. The organic layer was dried over Na$_2$SO$_4$ and the solvent was evaporated under reduced pressure followed by reverse-phase HPLC purification. LCMS m/z 470.9 (M+1). $^1$H NMR (400 MHz, DMSO-d$_6$) δ 12.56 (s, 1H), 9.23 (d, J=2.2 Hz, 1H), 8.45 (s, 1H), 8.31 (s, 1H), 8.22 (d, J=2.2 Hz, 1H), 7.23-7.10 (m, 2H), 4.84 (s, 2H), 3.64-3.45 (m, 8H). $^{19}$F NMR (376 MHz, DMSO-d$_6$) δ −150.43 (d, J=21.2 Hz), −155.78 (d, J=21.8 Hz).

N-((4,5-difluoro-1H-benzo[d]imidazol-2-yl)methyl)-2-morpholino-9-(thiazol-5-yl)-9H-purin-6-amine
(Compound 8)

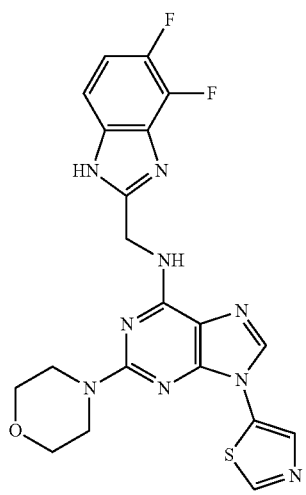 [SMILES: Fc1ccc2[nH]c(CNc3nc(N4CCOCC4)nc4c3ncn4-c3cncs3)nc2c1F]

Compound 8 was prepared as described in Scheme 2 using the same procedure as compound 4. LCMS m/z 470.4 (M+1). $^1$H NMR (400 MHz, DMSO-d$_6$) δ 12.54 (s, 1H), 9.00 (s, 1H), 8.46 (s, 1H), 8.37 (s, 2H), 7.27-7.08 (m, 2H), 4.94-4.67 (m, 2H), 3.53 (s, 8H). $^{19}$F NMR (376 MHz, DMSO-d$_6$) δ −150.40 (d, J=21.2 Hz), −155.77 (d, J=20.8 Hz).

N-((4,5-difluoro-1H-benzo[d]imidazol-2-yl)methyl)-2-morpholino-9-(thiazol-2-yl)-9H-purin-6-amine
(Compound 9)

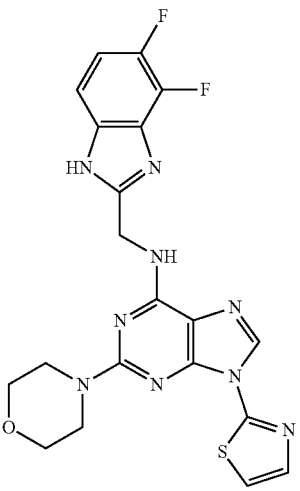 [SMILES: Fc1ccc2[nH]c(CNc3nc(N4CCOCC4)nc4c3ncn4-c3nccs3)nc2c1F]

Compound 9 was prepared as described in Scheme 2 using the same procedure as compound 4. LCMS m/z 470.5 (M+1). $^1$H NMR (400 MHz, DMSO-d$_6$) δ 12.58 (s, 1H), 8.54 (s, 1H), 8.45 (s, 1H), 7.71 (d, J=3.5 Hz, 1H), 7.66 (d, J=3.5 Hz, 1H), 7.25-7.06 (m, 2H), 4.84 (s, 2H), 3.67-3.49 (m, 8H). $^{19}$F NMR (376 MHz, DMSO-d$_6$) δ −150.36, −155.72.

N-(2,6-dichloro-5-nitropyrimidin-4-yl)-5-methylisoxazol-3-amine

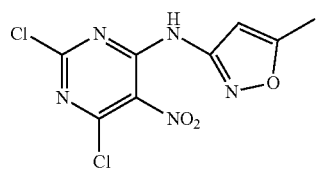 [SMILES: Cc1cc(Nc2nc(Cl)nc(Cl)c2[N+](=O)[O-])no1]

A magnetically stirred solution of 2,4,6-trichloro-5-nitropyrimidine (0.2 g, 0.876 mmol) and DIPEA (0.199 ml, 1.138 mmol)) in anhydrous 1,4-dioxane (3.50 ml) at 0° C. was treated dropwise with a solution of 5-methylisoxazol-3-amine (0.086 g, 0.876 mmol) in anhydrous 1,4-dioxane (0.5 mL). The resulting solution was stirred for 3 h at r.t. and concentrated under reduced pressure. The residue was subjected to flash column chromatography (silica gel, hexane:EtOAc, 5:1) Rf~0.42, yield 49%. LCMS m/z 290.2 (M+1).

2,6-dichloro-N$^4$-(5-methylisoxazol-3-yl)pyrimidine-4,5-diamine

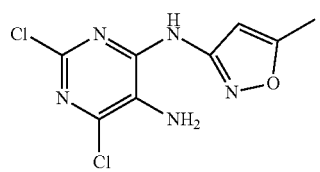

N-(2,6-dichloro-5-nitropyrimidin-4-yl)-5-methylisoxazol-3-amine (0.115 g, 0.396 mmol) was dissolved in acetic acid (1.586 ml) followed by addition of iron (0.221 g, 3.96 mmol) powder. Mixture was stirred vigorously for 30 min. Completion of the reaction was monitored by LCMS and crude product was subjected to flash column chromatography (silica gel, hexane:EtOAc, 2:1) Rf~0.35, yield 87%. LCMS m/z 260.4 (M+1).

3-(2,6-dichloro-9H-purin-9-yl)-5-methylisoxazole

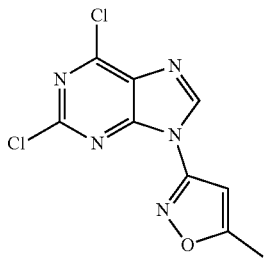 [SMILES: Cc1cc(-n2cnc3c(Cl)nc(Cl)nc32)no1]

2,6-dichloro-N4-(5-methylisoxazol-3-yl)pyrimidine-4,5-diamine (0.12 g, 0.461 mmol) was added to 2 ml MW vial. Next diethoxymethyl acetate (7.54 ml, 4.61 mmol) was added and reaction mixture was heated overnight at 80° C. The crude mixture was extracted with EtOAc and then washed with NaHCO$_3$, water, and brine. The organic layer was dried over Na$_2$SO$_4$ and the solvent was evaporated under reduced pressure followed by flash column chromatography (silica gel, hexane:EtOAc, 2:1). Rf~0.45, yield 92%. LCMS m/z 270.4 (M+1).

N-((4,5-difluoro-1H-benzo[d]imidazol-2-yl)methyl)-9-(5-methylisoxazol-3-yl)-2-morpholino-9H-purin-6-amine (Compound 3)

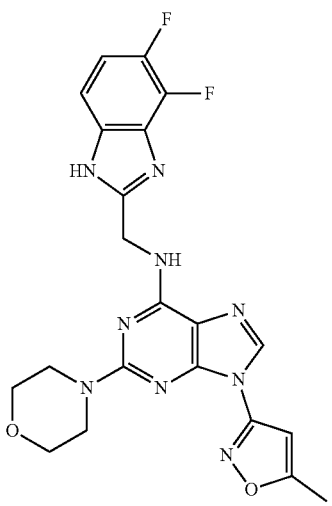 [SMILES: Cc1cc(-n2cnc3c(NCc4nc5c(F)c(F)ccc5[nH]4)nc(N4CCOCC4)nc32)no1]

Compound 3 was prepared as described in Scheme 3 (using the procedure for compound 5) starting from 3-(2,6-dichloro-9H-purin-9-yl)-5-methylisoxazole in 49% yield over two steps as a white solid. LCMS m/z 468.5 (M+1). $^1$H NMR (400 MHz, DMSO-d$_6$) δ 12.56 (s, 1H), 8.40 (s, 1H), 8.32 (s, 1H), 7.25-7.12 (m, 2H), 7.07 (s, 1H), 4.82 (s, 2H), 3.61-3.40 (m, 8H), 2.52 (s, 3H).

DOCUMENTS CITED

1. Bosken, C. A.; Farnung, L.; Hintermair, C.; Merzel Schachter, M.; Vogel-Bachmayr, K.; Blazek, D.; Anand, K.; Fisher, R. P.; Eick, D.; Geyer, M., The structure and substrate specificity of human Cdk12/Cyclin K. Nat. Commun. 2014, 5, 3505.

2. Bibian, M.; Rahaim, R. J.; Choi, J. Y.; Noguchi, Y.; Schurer, S.; Chen, W.; Nakanishi, S.; Licht, K.; Rosenberg, L. H.; Li, L.; Feng, Y.; Cameron, M. D.; Duckett, D. R.; Cleveland, J. L.; Roush, W. R., Development of highly selective casein kinase 1delta/1epsilon (CK1delta/epsilon) inhibitors with potent antiproliferative properties. Bioorg. Med. Chem. Lett. 2013, 23 (15), 4374-80.

3. Niu, H. Y.; Xia, C.; Qu, G. R.; Zhang, Q.; Jiang, Y.; Mao, R. Z.; Li, D. Y.; Guo, H. M., CuBr catalyzed C—N cross coupling reaction of purines and diaryliodonium salts to 9-arylpurines. Org. Biomol. Chem. 2011, 9 (14), 5039-42.

4. Ding, S.; Gray, N. S.; Ding, Q.; Schultz, P. G., Expanding the diversity of purine libraries. Tetrahedron Lett. 2001, 42 (50), 8751-8755.

5. Bielawski, M.; Aili, D.; Olofsson, B., Regiospecific one-pot synthesis of diaryliodonium tetrafluoroborates from arylboronic acids and aryl iodides. J. Org. Chem. 2008, 73 (12), 4602-4607.

6. Bielawski, M.; Malmgren, J.; Pardo, L. M.; Wikmark, Y.; Olofsson, B., One-pot synthesis and applications of N-heteroaryl iodonium salts. ChemistryOpen 2014, 3 (1), 19-22.

7. Monastyrskyi, A.; Nilchan, N.; Quereda, V.; Noguchi, Y.; Ruiz, C.; Grant, W.; Cameron, M.; Duckett, D.; Roush, W., Development of dual casein kinase 1delta/1epsilon (CK1delta/epsilon) inhibitors for treatment of breast cancer. Bioorg. Med. Chem. 2017.

All patents and publications referred to herein are incorporated by reference herein to the same extent as if each individual publication was specifically and individually indicated to be incorporated by reference in its entirety.

What is claimed is:

1. A method of inhibiting a cyclin-dependent kinase, comprising contacting the cyclin-dependent kinase and an effective amount or concentration of a compound of formula (I)

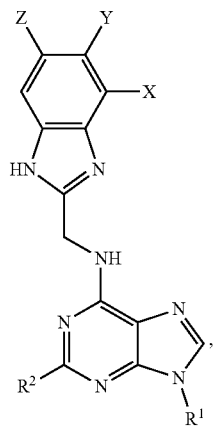

wherein

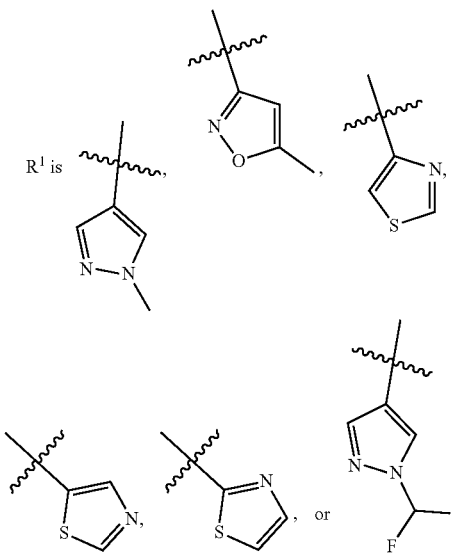

wherein a wavy line indicates a position of bonding; $R^2$ is $NR^3R^4$, wherein $R^3$ and $R^4$ are each independently H or (C1-C6)alkyl, the alkyl being optionally substituted with hydroxyl or with $N(R^6)_2$ on any carbon atom thereof other than a carbon atom bonded directed to the nitrogen atom of $NR^3R^4$, or $R^3$ and $R^4$ together with the nitrogen atom to which they are bonded form a 5- to 7-membered heterocyclyl ring optionally comprising 1 or 2 additional heteroatoms selected from the group consisting of O, S, and $NR^5$, wherein $R^5$ is H or (C1-C6)alkyl, the alkyl being optionally substituted with hydroxyl or with $N(R^6)_2$ on any carbon atom thereof other than a carbon atom bonded directed to the nitrogen atom of $NR^5$, wherein the heterocyclyl ring is further optionally mono- or independently multi-substituted with (C1-C6)alkyl, the alkyl being optionally substituted with hydroxyl or with $N(R^6)_2$, wherein each $R^6$ is independently H or (C1-C6)alkyl;

X, Y and Z are independently hydrogen, fluoro, chloro, methoxy, CN, $NO_2$, $CF_3$, NHCOR, lower alkyl, $C(R')_2NR_2$, $C(R')_2OH$, $C(R')_2OR$, $CO_2R$, $CONR_2$;

R is independently at each occurrence selected from the group consisting of hydrogen, deuterium, alkyl, cycloalkyl, cycloalkylalkyl, aryl, aralkyl, heterocyclyl, heterocyclylalkyl, heteroaryl, and heteroarylalkyl; or wherein two R groups together with a nitrogen atom or with two adjacent nitrogen atoms to which they are bonded can together form a $(C_{3-8})$ heterocyclyl optionally further comprising 1-3 additional heteroatoms selected from the group consisting of O, N, S, S(O) and $S(O)_2$;

R' is H or (C1-C4)alkyl;

or a pharmaceutically acceptable salt thereof.

2. The method of claim 1, wherein $R^2$ is a group of formula

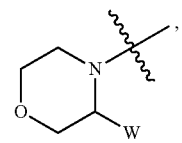

wherein W is H or (C1-C6)alkyl, wherein the alkyl is optionally further substituted with hydroxyl or $N(R^7)_2$, wherein each $R^7$ is independently H or (C1-C6)alkyl or where $N(R^7)_2$ is a 5-, 6-, or 7-membered heterocyclyl ring, wherein a wavy line indicates a position of bonding.

3. The method of claim 1, wherein the compound of formula (I) is any one of the following compounds:
Compound 1
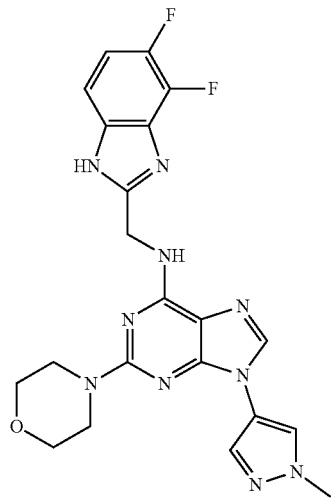
Compound 2
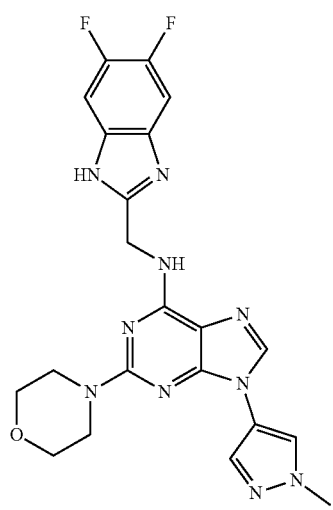
Compound 3
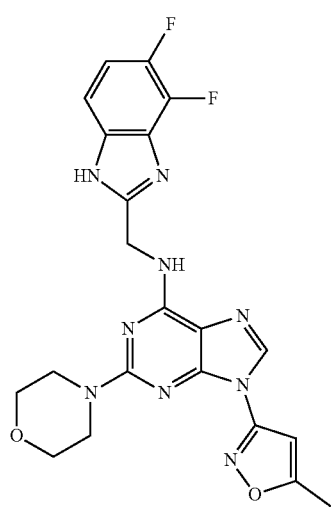
Compound 4
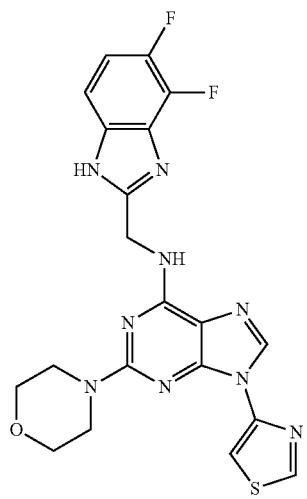
Compound 5
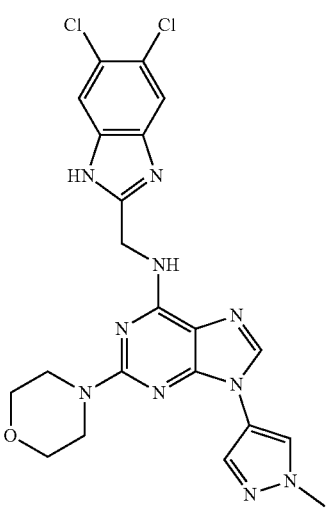
Compound 6
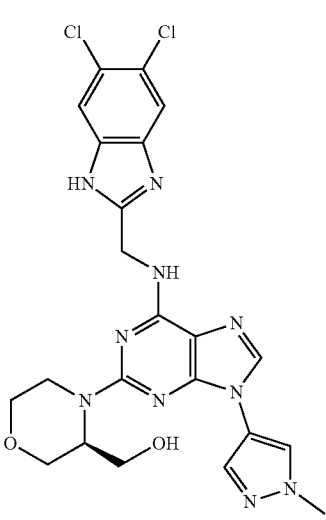

Compound 7

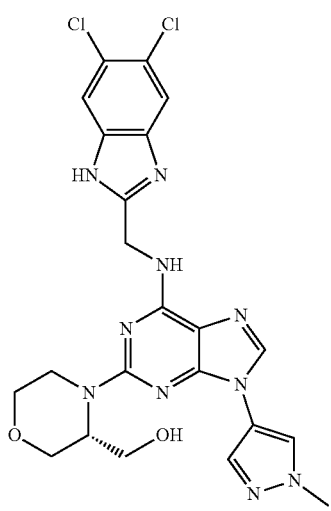

Compound 8

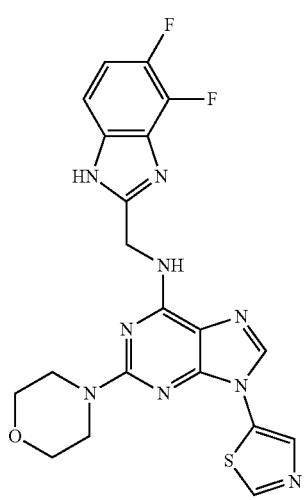

Compound 9

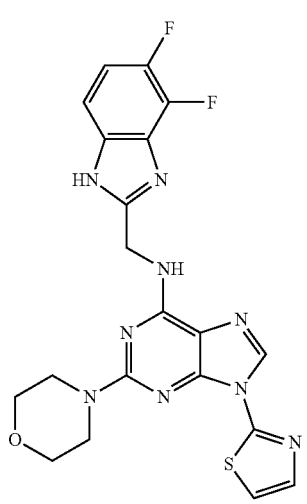

Compound 10

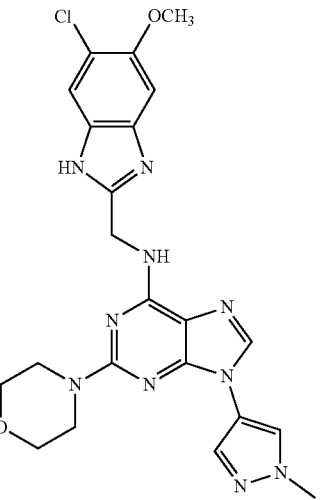

Compound 11

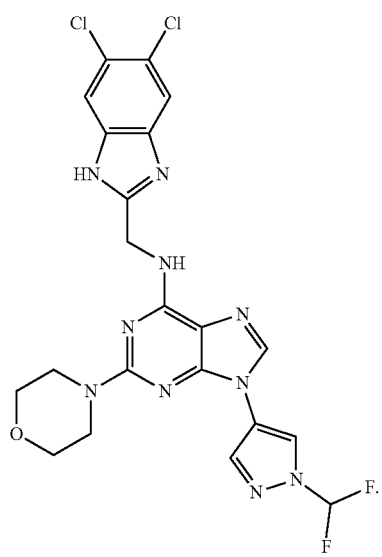

4. The method of claim 1, wherein the cyclin-dependent kinase is cyclin-dependent kinase12 or 13 (CDK12 or CDK13).

5. The method of claim 1, wherein the compound of formula (I) is not an effective inhibitor of casein kinase 1δ or 1ε (CK1δ/ε).

6. The method of claim 1, wherein the cyclin-dependent kinase is disposed within the body tissue of a patient afflicted with cancer.

7. A method of treating a cancer in a patient afflicted therewith, comprising administering to the patient an effective dose of a compound of formula (I)

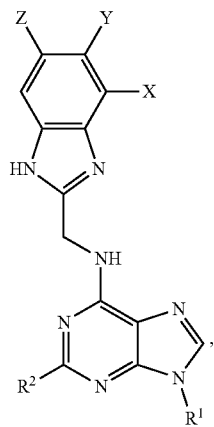

wherein

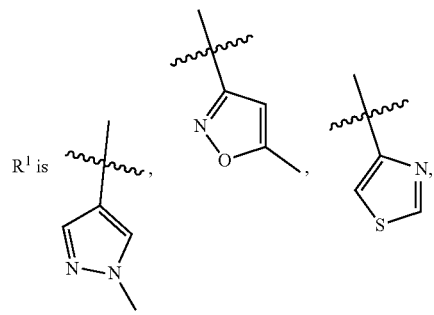

$R^1$ is

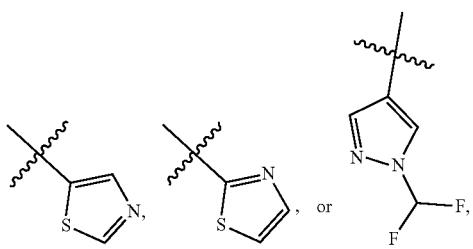

or wherein a wavy line indicates a position of bonding;
$R^2$ is $NR^3R^4$, wherein $R^3$ and $R^4$ are each independently H or (C1-C6)alkyl, the alkyl being optionally substituted with hydroxyl or with $N(R^6)_2$ on any carbon atom thereof other than a carbon atom bonded directed to the nitrogen atom of $NR^3R^4$, or $R^3$ and $R^4$ together with the nitrogen atom to which they are bonded form a 5- to 7-membered heterocyclyl ring optionally comprising 1 or 2 additional heteroatoms selected from the group consisting of O, S, and $NR^5$, wherein $R^5$ is H or (C1-C6)alkyl, the alkyl being optionally substituted with hydroxyl or with $N(R^6)_2$ on any carbon atom thereof other than a carbon atom bonded directed to the nitrogen atom of $NR^5$, wherein the heterocyclyl ring is further optionally mono- or independently multi-substituted with (C1-C6)alkyl, the alkyl being optionally substituted with hydroxyl or with $N(R^6)_2$, wherein each $R^6$ is independently H or (C1-C6)alkyl;

X, Y and Z are independently hydrogen, fluoro, chloro, methoxy, CN, $NO_2$, $CF_3$, NHCOR, lower alkyl, $C(R')_2NR_2$, $C(R')_2OH$, $C(R')_2OR$, $CO_2R$, $CONR_2$;

R is independently at each occurrence selected from the group consisting of hydrogen, deuterium, alkyl, cycloalkyl, cycloalkylalkyl, aryl, aralkyl, heterocyclyl, heterocyclylalkyl, heteroaryl, and heteroarylalkyl; or wherein two R groups together with a nitrogen atom or with two adjacent nitrogen atoms to which they are bonded can together form a $(C_{3-8})$ heterocyclyl optionally further comprising 1-3 additional heteroatoms selected from the group consisting of O, N, S, S(O) and $S(O)_2$;

R' is H or (C1-C4)alkyl;

or a pharmaceutically acceptable salt thereof.

8. The method of claim 7, wherein $R^2$ is a group of formula

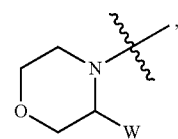

wherein W is H or (C1-C6)alkyl, wherein the alkyl is optionally further substituted with hydroxyl or $N(R^7)_2$, wherein each $R^7$ is independently H or (C1-C6)alkyl or where $N(R^7)_2$ is a 5-, 6-, or 7-membered heterocyclyl ring, wherein a wavy line indicates a position of bonding.

9. The method of claim 7, wherein the compound of formula (I) is any one of the following compounds:

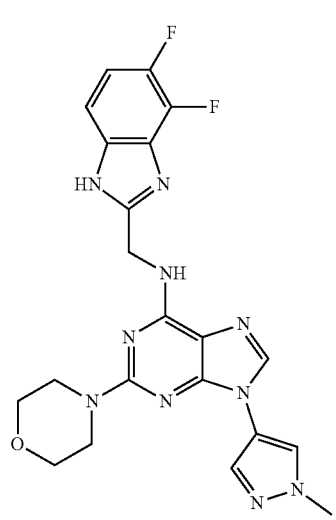

Compound 1

Compound 2
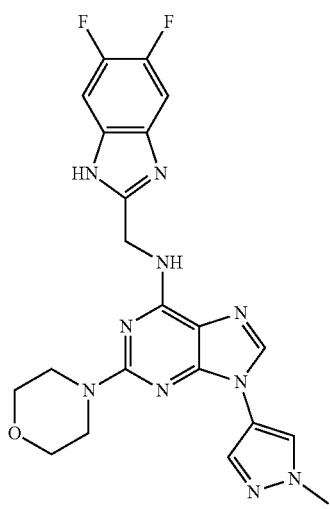
Compound 3
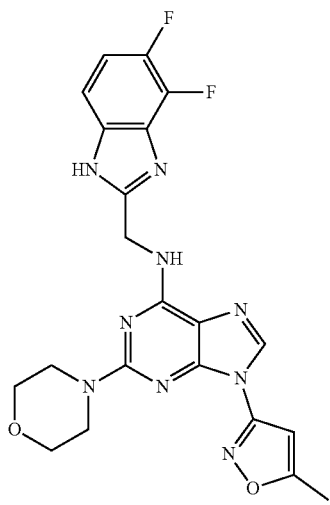
Compound 4
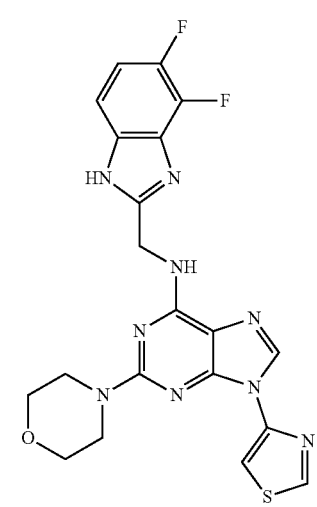
Compound 5
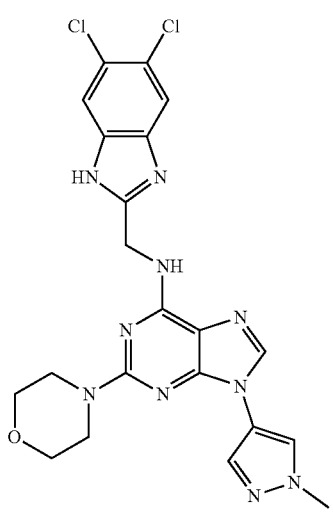
Compound 6
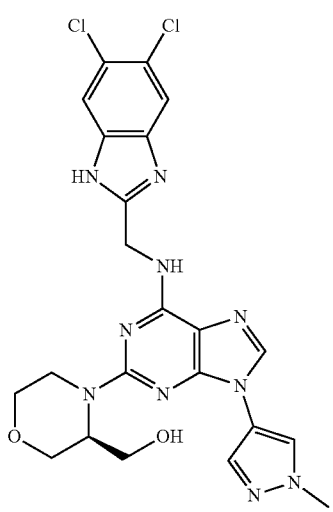
Compound 7
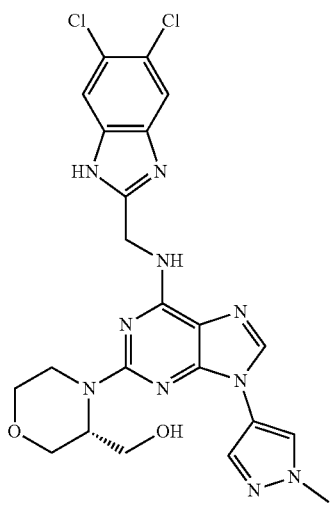

Compound 8
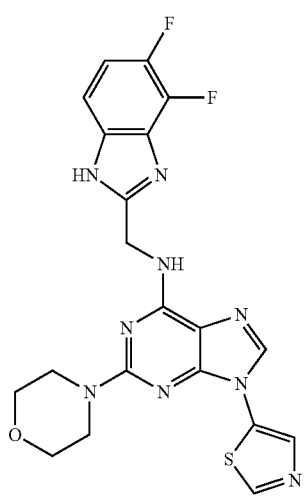
Compound 9
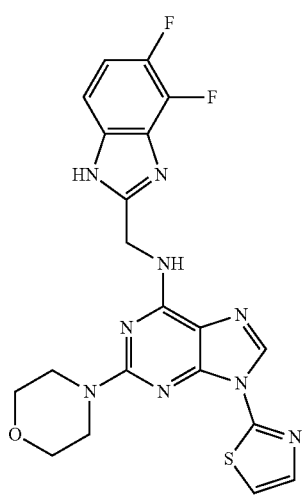
Compound 10
Compound 11
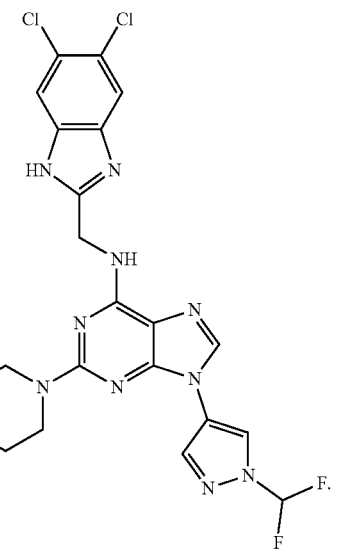
10. The method of claim 7, wherein the compound of formula (I) is not an effective inhibitor of casein kinase 1δ or 1ε (CK1δ/ε).
11. The method of claim 7 wherein the cancer is breast cancer, brain cancer or ovarian cancer.
12. A compound of formula (I)
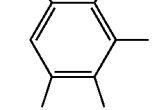
wherein
$R^1$ is 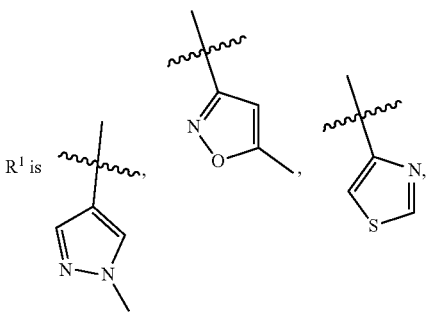

-continued

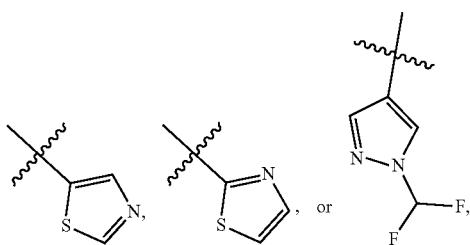

wherein a wavy line indicates a position of bonding;

R² is NR³R⁴, wherein R³ and R⁴ are each independently H or (C1-C6)alkyl, the alkyl being optionally substituted with hydroxyl or with N(R⁶)₂ on any carbon atom thereof other than a carbon atom bonded directed to the nitrogen atom of NR³R⁴, or R³ and R⁴ together with the nitrogen atom to which they are bonded form a 5- to 7-membered heterocyclyl ring optionally comprising 1 or 2 additional heteroatoms selected from the group consisting of O, S, and NR⁵, wherein R⁵ is H or (C1-C6)alkyl, the alkyl being optionally substituted with hydroxyl or with N(R⁶)₂ on any carbon atom thereof other than a carbon atom bonded directed to the nitrogen atom of NR⁵, wherein the heterocyclyl ring is further optionally mono- or independently multi-substituted with (C1-C6)alkyl, the alkyl being optionally substituted with hydroxyl or with N(R⁶)₂, wherein each R⁶ is independently H or (C1-C6)alkyl;

X, Y and Z are independently hydrogen, fluoro, chloro, methoxy, CN, NO₂, CF₃, NHCOR, lower alkyl, C(R')₂NR₂, C(R')₂OH, C(R')₂OR, CO₂R, CONR₂;

R is independently at each occurrence selected from the group consisting of hydrogen, deuterium, alkyl, cycloalkyl, cycloalkylalkyl, aryl, aralkyl, heterocyclyl, heterocyclylalkyl, heteroaryl, and heteroarylalkyl; or wherein two R groups together with a nitrogen atom or with two adjacent nitrogen atoms to which they are bonded can together form a (C₃₋₈) heterocyclyl optionally further comprising 1-3 additional heteroatoms selected from the group consisting of O, N, S, S(O) and S(O)₂;

R' is H or (C1-C4)alkyl;

or a pharmaceutically acceptable salt thereof.

13. The compound of claim 12, wherein R² is a group of formula

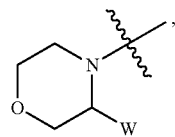

wherein W is H or (C1-C6)alkyl, wherein the alkyl is optionally further substituted with hydroxyl or N(R⁷)₂, wherein each R⁷ is independently H or (C1-C6)alkyl or where N(R⁷)₂ is a 5-, 6-, or 7-membered heterocyclyl ring, wherein a wavy line indicates a position of bonding.

14. The compound of claim 12, wherein the compound of formula (I) is any one of the following compounds:

Compound 1

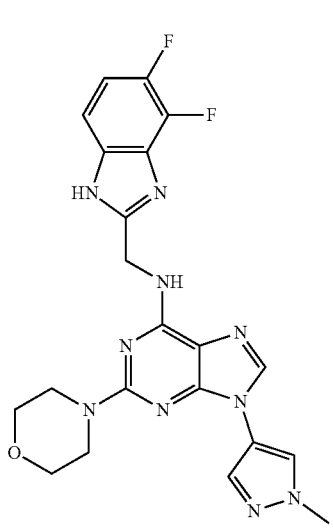

Compound 2

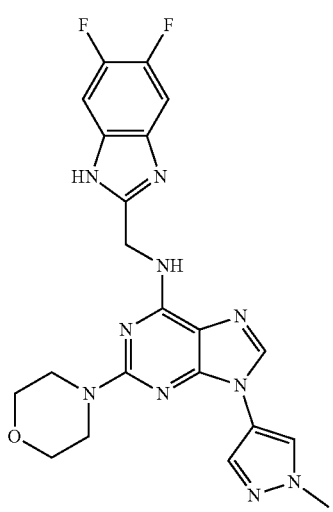

Compound 3

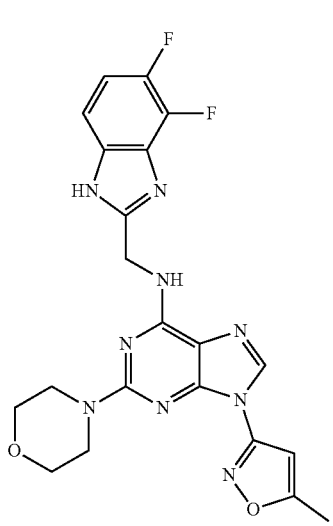

Compound 4
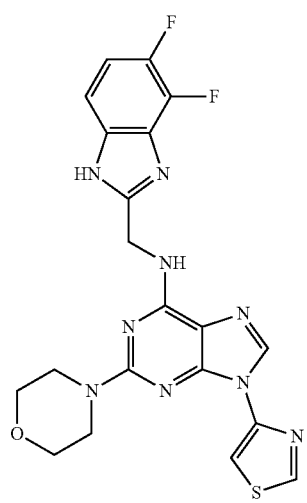
Compound 5
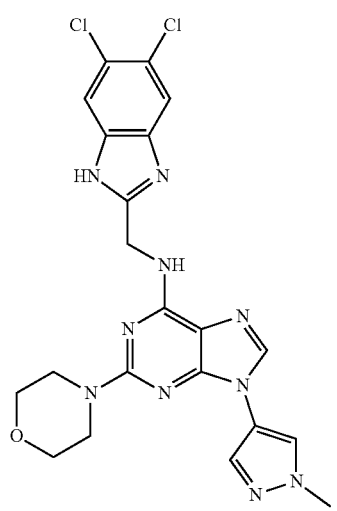
Compound 6
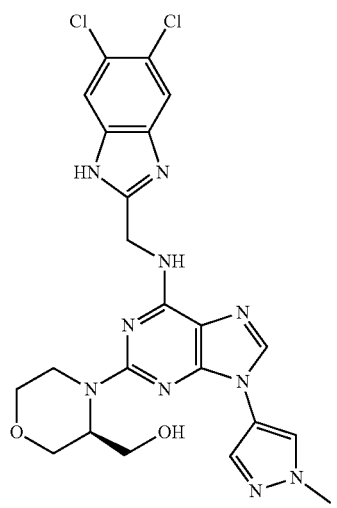
Compound 7
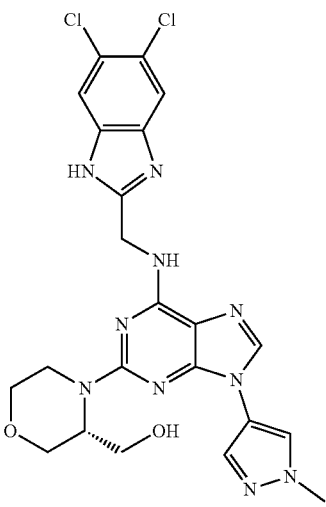
Compound 8
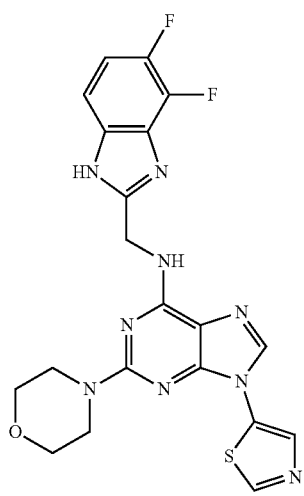
Compound 9

Compound 10
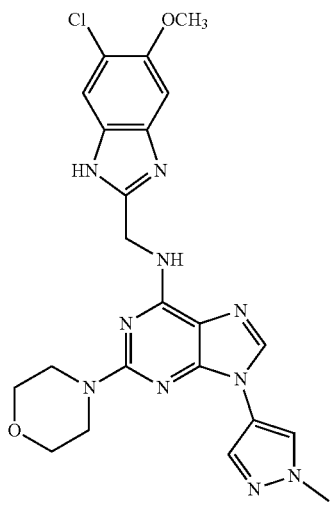
Compound 11
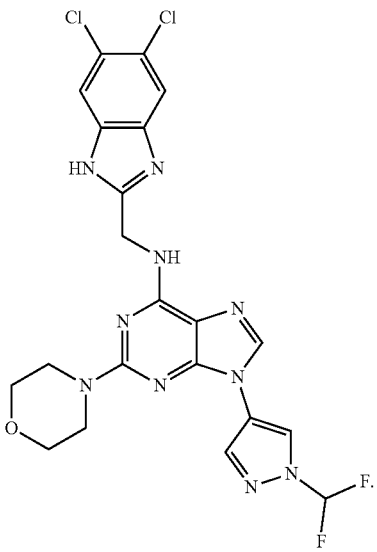
* * * * *

SEQUENCE LISTING

```
<160> NUMBER OF SEQ ID NOS: 8

<210> SEQ ID NO 1
<211> LENGTH: 20
<212> TYPE: DNA
```

```
<213> ORGANISM: Artificial sequence
<220> FEATURE:
<223> OTHER INFORMATION: Synthetic

<400> SEQUENCE: 1
tggctcagct agaactgatc                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
atatatggac catgatctga                                              20

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
ccaatctgga actggctcag                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
caagtgctgc agaaggaatg                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic

<400> SEQUENCE: 5
ggtgtttgaa tatatggacc                                              20

<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
caagtccaaa gtctgcaagt t                                            21

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
tcaccagggc tgcttttaac                                              20
```

```
<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
atctcgctcc tggaagatgg                                              20
```